United States Patent
Litke et al.

(10) Patent No.: US 11,607,210 B2
(45) Date of Patent: Mar. 21, 2023

(54) AUTO-LOCKING WOUND RETRACTOR

(71) Applicant: Intuitive Surgical Operations, Inc., Sunnyvale, CA (US)

(72) Inventors: Ronald G. Litke, Sandy Hook, CT (US); Jake A. Luckman, New Haven, CT (US); Jeffrey R. Roeder, Alameda, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 0 days.

(21) Appl. No.: 17/200,483

(22) Filed: Mar. 12, 2021

(65) Prior Publication Data

US 2021/0282760 A1   Sep. 16, 2021

Related U.S. Application Data

(60) Provisional application No. 62/988,894, filed on Mar. 12, 2020.

(51) Int. Cl.
*A61B 17/02* (2006.01)
*A61B 17/00* (2006.01)

(52) U.S. Cl.
CPC ...... *A61B 17/0293* (2013.01); *A61B 17/0218* (2013.01); *A61B 2017/00371* (2013.01)

(58) Field of Classification Search
CPC ............ A61B 17/0293; A61B 17/3423; A61B 17/0218; A61B 17/3462
USPC .................................................. 600/184–249
See application file for complete search history.

(56) References Cited

U.S. PATENT DOCUMENTS

| | | | | |
|---|---|---|---|---|
| 5,524,644 A | * | 6/1996 | Crook | A61B 17/3423 602/43 |
| 9,707,011 B2 | * | 7/2017 | Malkowski | A61B 17/3423 |
| 2004/0012209 A1 | | 1/2004 | Liu et al. | |
| 2004/0073090 A1 | | 4/2004 | Butler et al. | |
| 2004/0154624 A1 | * | 8/2004 | Bonadio | A61B 17/3423 128/849 |
| 2006/0161050 A1 | | 7/2006 | Butler et al. | |

(Continued)

FOREIGN PATENT DOCUMENTS

WO   WO-2007044911 A1   4/2007

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ USA 1986, vol. 3A, 332 pages.

(Continued)

*Primary Examiner* — Eduardo C Robert
*Assistant Examiner* — Tara Rose E Carter
(74) *Attorney, Agent, or Firm* — Schwegman, Lundberg & Woessner, P.A.

(57) ABSTRACT

A wound retractor includes a sleeve with proximal and distal ends, an inner ring inside the sleeve between the proximal and distal ends, and an outer ring outside the sleeve between the proximal and distal ends. The inner ring includes a tapered outer surface that increases in diameter from a proximal end of the inner ring toward a distal end of the inner ring. The outer ring includes a tapered inner surface that increases in diameter from a proximal end of the outer ring toward a distal end of the outer ring. A portion of the sleeve is captured between the tapered outer surface and the tapered inner surface.

20 Claims, 19 Drawing Sheets

(56) References Cited

U.S. PATENT DOCUMENTS

| | | | |
|---|---|---|---|
| 2007/0088241 A1 | 4/2007 | Brustad et al. | |
| 2007/0225569 A1* | 9/2007 | Ewers | A61B 17/3423 600/206 |
| 2009/0187079 A1 | 7/2009 | Albrecht et al. | |
| 2011/0071359 A1 | 3/2011 | Bonadio et al. | |
| 2019/0159769 A1 | 5/2019 | Ortiz et al. | |
| 2019/0350620 A1 | 11/2019 | Patel et al. | |
| 2021/0282761 A1 | 9/2021 | Luckman et al. | |

OTHER PUBLICATIONS

U.S. Appl. No. 17/200,495, filed Mar. 12, 2021, Wound Retractor Clamp.

* cited by examiner

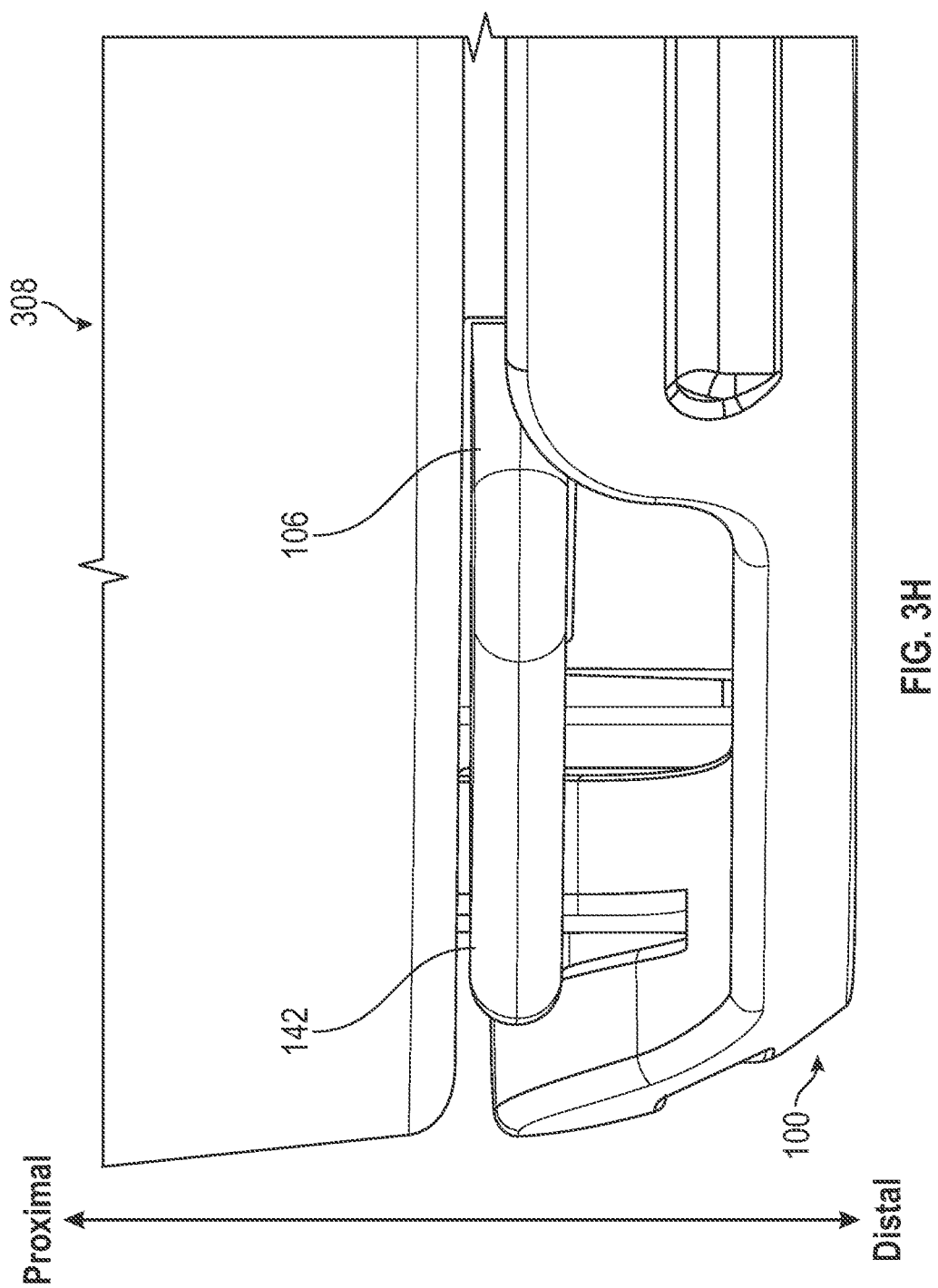

AUTO-LOCKING WOUND RETRACTOR

CLAIM OF PRIORITY

This application claims the benefit of priority under 35 U.S.C. § 119(e) to U.S. Patent Application Ser. No. 62/988,894, filed on Mar. 12, 2020, which is incorporated by reference herein in its entirety.

TECHNICAL FIELD

This document relates generally to medical devices, and more particularly, to surgical wound retractors for use in minimally invasive surgical procedures.

BACKGROUND

Surgical systems that operate at least in part with computer-assisted control ("telesurgical systems"), such as those employed for minimally invasive medical procedures, can include large and complex equipment to precisely control relatively small instruments. Such systems are sometimes referred to as robotic surgical systems or surgical robots. The da Vinci® Surgical Systems commercialized by Intuitive Surgical, Inc. are examples of telesurgical systems.

Various telesurgical system architectures exist. Some system architectures enable multiple (e.g., two, three, four, or more) surgical instruments to enter the body through a single body opening (surgical incision or natural orifice), and these systems are sometimes referred to as "single-port" systems (e.g., the da Vinci SP® Surgical System). Other system architectures enable multiple surgical instruments to enter the body individually at corresponding multiple locations, and these systems are sometimes referred to as "multi-port" systems (e.g., the da Vinci Xi® Surgical System). Persons of skill in the art will understand that multi-port systems may sometimes be configured during surgery to operate through a single natural body orifice, such as the mouth or anus, or through a single incision (e.g., Intuitive Surgical's Single Site® technology used with a da Vinci Xi® Surgical System). Persons of skill in the art will also understand that single- and multi-port configurations may be combined simultaneously in a single telesurgical system (e.g., two or more instruments inserted via one body opening, and one or more other instruments inserted via one or more corresponding other body openings).

Surgical instruments used during minimally invasive surgery typically include an endoscopic camera or therapeutic end effector mounted at the end of a long, slender instrument shaft. Since instrument end effectors are typically located deep within the body during surgery, telesurgical systems are designed to constrain rotation of the instrument at a point located on the instrument's shaft, often referred to as a remote center of motion. Either kinematic hardware structure or control system software design (or a combination of the two) may be used to impose this remote center of motion constraint. To minimize tissue trauma during surgery, the constrained remote center of motion is typically located at or near the body opening through which the instrument enters.

If a telesurgical system is to be used at or near the body opening, however, then several challenges exist. First, to provide sufficient distance between an instrument's constrained remote center of motion and its end effector, the constrained remote center of motion may need to be located proximally of the body opening, sometimes by several centimeters or more. Second, if part of the surgery is performed proximally of the ultimate surgical site (e.g., using the telesurgical system to perform dissection to reach the ultimate surgical site), there needs to be an easy way to relocate the constrained remote center of motion distally as the surgery progresses towards the deepest surgical site in the patient's body.

A third challenge exists if insufflation is to be used in the body cavity in which the ultimate surgical site is located (e.g., the abdomen, the rectum, among other example sites). When the constrained remote center of motion is located at the patient's body wall, and when cannulas are used to introduce instruments past the body wall, seals in the cannulas are used to maintain insufflation gas pressure within the body cavity both when an instrument is inserted through the body wall via the cannula and when the instrument is removed from the cannula. But if the cannula is located proximal of the body opening, insufflation gas pressure must still be maintained.

Further, for a single-port system in which two or more instruments can be introduced into a patient and moved as a single instrument cluster, these challenges become more complex because the constrained remote centers of motion for the two or more instruments are located at the same point or close to one another. In addition, single-port system instruments may be designed with joints that allow them to be inserted close to one another, but then individually spread apart after passing beyond the body wall to provide triangulation to more effectively perform surgery. And, a further challenge exists during the use of a single-port system if an additional instrument (either a telesurgical system instrument or a manually operated instrument) is to be introduced to assist the surgery, because the cluster of single-port system instruments blocks some access locations of the additional instrument.

To address the foregoing challenges with locating and changing the remote center of motion and with maintaining insufflation gas pressure, a single-port or multi-port telesurgical system may employ an instrument access device with an inflatable envelope that effectively extends the pressurized zone of insufflation gas outside of the body and above/around the surgical site incision. The pressurized and sealed envelope cavity provides an operating space for arms/shafts of multiple instruments of a teleoperated surgical system to articulate outside the body such that instrument end effectors are located at or near the surface of the body at the incision site of the wound retractor coupled to the instrument access device.

Retraction and isolation of a surgical incision is an important element associated with a surgical procedure, and is commonly accomplished using a circumferential wound retraction device. Additionally, in the case of teleoperated surgical systems, the wound retractor needs to be configured to connect with and seal to an instrument access device, for example, including such instrument access devices described above for a single-port or multi-port telesurgical systems that will be employed to conduct surgery at or near the incision/outside of the patient's body.

SUMMARY

Examples according to this disclosure include a wound retractor. The wound retractor includes a sleeve with proximal and distal ends, an inner ring inside the sleeve between the proximal and distal ends, and an outer ring outside the sleeve between the proximal and distal ends. The inner ring includes a tapered outer surface that increases in diameter from a proximal end of the inner ring toward a distal end of the inner ring. The outer ring includes a tapered inner surface that increases in diameter from a proximal end of the outer ring toward a distal end of the outer ring. A portion of the sleeve is captured between the tapered outer surface and the tapered inner surface.

An example medical device includes a wound retractor and an access port assembly. The wound retractor includes a sleeve, an inner ring inside the sleeve, an outer ring outside the sleeve, and a housing in which the inner and outer rings are captured. The inner ring includes a tapered outer surface having a proximal diameter and a distal diameter. The proximal diameter of the tapered outer surface is less than the distal diameter of the tapered outer surface. The outer ring includes a tapered inner surface having a proximal diameter and a distal diameter. The proximal diameter of the tapered inner surface is less than the distal diameter of the tapered inner surface. A portion of the sleeve is captured between the tapered outer surface and the tapered inner surface. The access port assembly includes an envelope comprising a distal end, and a clamp connected to the distal end of the envelope and configured to be connected to the housing of the wound retractor.

In an example, a medical device (for which a distal direction is defined towards a patient and a proximal direction is defined away from the patient) includes an inner ring comprising an outer surface tapering outward in the distal direction, an outer ring surrounding the inner ring and comprising an inner surface tapering outward in the distal direction and opposing the outer surface of the inner ring, and a wound retractor sleeve captured between the outer surface of the inner ring and the inner surface of the outer ring.

BRIEF DESCRIPTION OF THE DRAWINGS

In the drawings, which are not necessarily to scale, like numerals describe similar components in different views. Like numerals having different letter suffixes represent different instances of similar components. The drawings illustrate generally, by way of example, but not by way of limitation, various embodiments discussed in this document.

FIGS. 3E-3H depict connecting an example clamp to an example wound retractor in accordance with this disclosure.

DETAILED DESCRIPTION

Figure 1A:
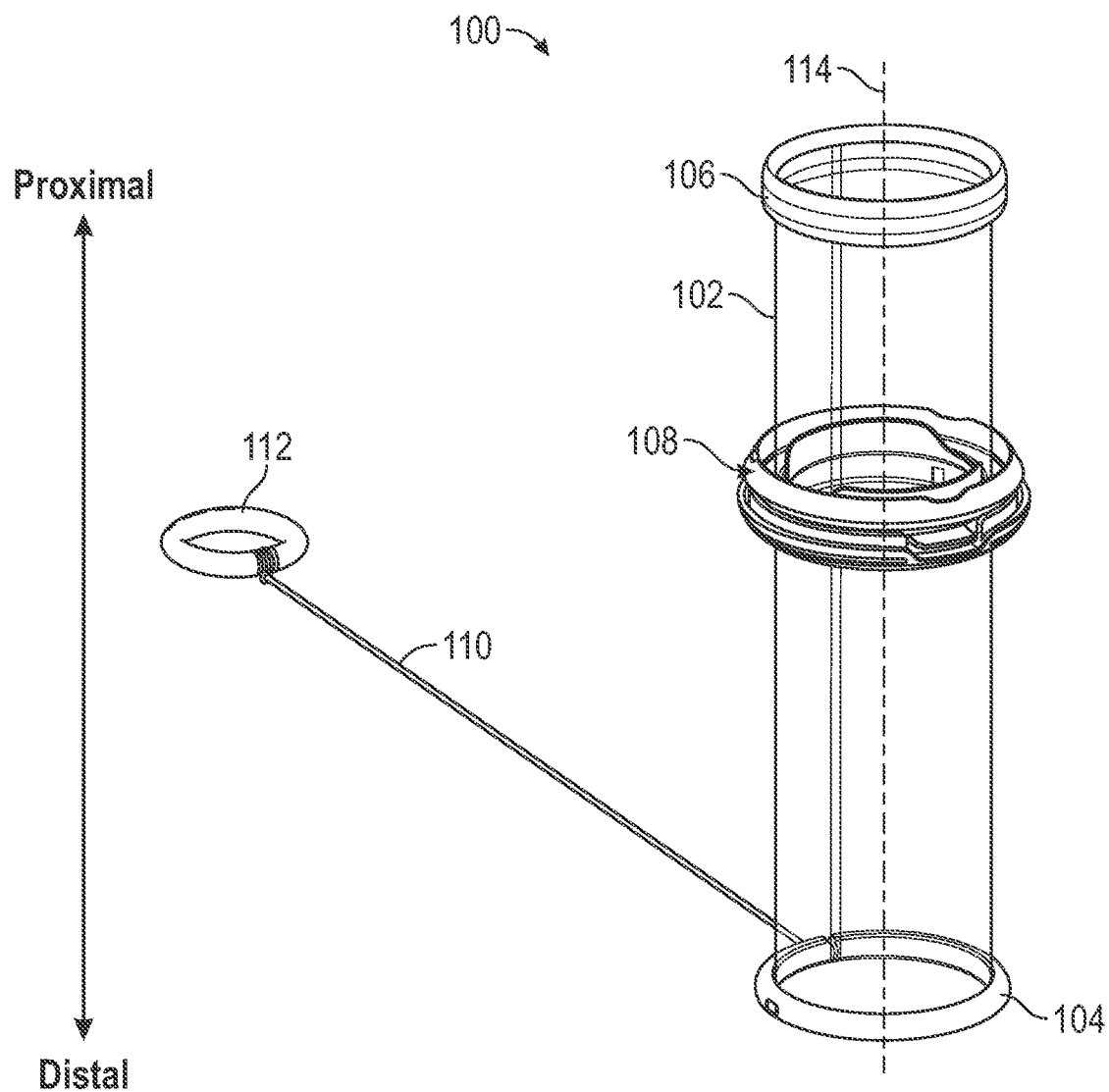
FIG. 1A is a perspective view depicting example wound retractor 100 in accordance with this disclosure.

FIG. 1A is a perspective view depicting example wound retractor 100 in accordance with this disclosure. During some surgical procedures, wound retractors are used to seal the incision and hold the incised edges of the incision in an open position. Use of wound retractors during surgical procedures, including, for example, during teleoperated surgical procedures, may provide protection against infection and prevent or protect against trauma to the incision and surrounding body wall. Wound retractors often do not include structures for maintaining insufflation pressure or sealing the surgical site against contaminants. As such, wound retractors can be made to be coupled to an instrument access port device to establish and maintain insufflation pressure and to seal the surgical site against contaminants.

In FIG. 1A, wound retractor 100 includes sleeve 102 having distal ring 104 and proximal ring 106, auto-locking collar 108, removal tether 110 and removal ring 112. Sleeve 102 can be a flexible and/or elastic annular sheath that can have a generally cylindrical configuration disposed along longitudinal axis 114. Sleeve 102 can be made from a variety of polymers, including, for example, a variety of polyurethane plastics. In one example, sleeve 102 is made from a thermoplastic polyurethane (TPU) film. In one example, sleeve 102 is made from a polyether based TPU, which may exhibit superior microbial resistance than other types of TPUs (e.g., polyester based TPUs).

Sleeve 102 can have elastic properties to allow the sleeve to be stretched between distal and proximal rings 104 and 106 to apply a retraction force on and to thereby dilate the incision to a target size (e.g., diameter). However, the elasticity of sleeve 102 may be relatively small, in some examples. The material of sleeve 102 may be chosen, for example, because it is not overly stretchy/elastic. Films that are too elastic may make it too difficult to open the incision because the film won't transmit enough of the axial tension in sleeve 102 to radial forces that open the walls of the incision. Thus, the material of sleeve 102 may have properties that are selected to strike a balance between resistance to elastic stretching in order to easily hold open the incision, but still possessing enough elasticity to stretch around small features of, for example, distal ring 104, proximal ring 106, and/or auto-locking collar 108.

Distal and proximal rings 104 and 106 are, in the view of FIG. 1A, disposed in respective planes parallel to one another at the distal and proximal ends of sleeve 102 and extending radially from axis 114. Distal and proximal rings 104 and 106 can be made from a variety of materials, including a variety of different polymers. Rings 104 and 106 can be semi-rigid with enough flexibility to manipulate the rings to place wound retractor 100 within an incision in the body wall of a patient, for example, by deforming distal ring 104 to insert through the incision. Distal ring 104 can have a diameter greater than that desired for the incision and is configured to be inserted through the incision and rest against an inside surface of the body wall. Proximal ring 106 can have a diameter greater than that desired for the incision and is configured to be rolled over itself and sleeve 102 and around axis 114 and be placed outside of the incision. Distal and proximal rings 104 and 106 can be connected to sleeve 102 in a variety of ways. For example, distal and proximal rings 104 and 106 can be impulse welded to sleeve 102. In an example, distal and proximal rings 104 and 106 can be ultrasonically welded to sleeve 102. In another example, one or both of rings 104 and 106 can be connected to sleeve 102 by heat sealing and/or using an adhesive.

Auto-locking collar 108 is disposed along sleeve 102 between distal ring 104 and proximal ring 106. Auto-locking collar 108 is configured to freely slide along sleeve 102 in one direction and to automatically lock against movement along sleeve in an opposite direction. For example, in the example of FIG. 1A, collar 108 is configured to slide in a direction from proximal to distal ends of sleeve 102 to draw collar 108 closer to the site of the incision and closer to distal ring 104. Auto-locking collar 108 is also configured to automatically lock against movement of the collar in a direction from distal to proximal ends of sleeve 102. As will be described in greater detail with reference to FIGS. 1B-1G, collar 108 is configured to slide down sleeve 102 to be seated outside of the incision and against the outer surface of the body wall. Collar 108 can be slid down against the body wall and can be automatically locked in place to apply a force on sleeve 102 as the sleeve is tensioned between collar 108 and distal ring 104. Tensioning sleeve 102 between collar 108 and distal ring 104 applies a retraction force on and thereby dilates the incision.

As described in detail with reference to FIGS. 1E-1G, in an example, auto-locking collar 108 can include an inner ring inside sleeve 102. The inner ring includes a tapered outer surface, which increases in diameter from a proximal end of the inner ring toward a distal end of the inner ring. Auto-locking collar 108 can also include an outer ring outside the sleeve. The outer ring includes a tapered inner surface. The tapered inner surface of the outer ring increases in diameter from a proximal end of the outer ring toward a distal end of the outer ring. A portion of sleeve 102 is captured between the tapered outer surface and the tapered inner surface. Auto-locking collar 108 is configured to slide along sleeve 102 in a proximal-to-distal direction without causing the tapered outer surface and the tapered inner surface to lock onto sleeve 102. In response to a tensioning force on sleeve 102, however, the tapered outer surface and the tapered inner surface are configured to automatically lock onto the sleeve and to prevent collar 108 from moving relative to sleeve 102.

Referring to FIG. 1A again, removal tether 110 is connected to distal ring 104 at one end and to removal ring 112 at the opposite end. Removal tether can be fabricated from a variety of threads, rope, webbing, among other examples. In one example, removal tether 110 includes a size 5 braided suture. Removal ring 112 can be fabricated from a variety of materials, including a variety of polymers. After wound retractor 100 has been employed in a procedure, the retractor may be removed by pulling on tether 110 with ring 112, which, in turn, pulls distal ring 104 out of the body through the incision.

Figure 1B:
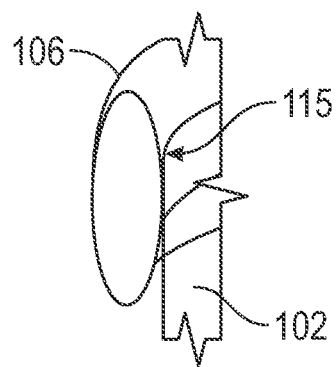
FIG. 1B is a section view depicting details of a proximal ring of the wound retractor of FIG. 1A.

FIG. 1B is a section view depicting details of proximal ring 106 of wound retractor 100. In FIG. 1B, proximal ring 106 includes an oblate shape including a flat or planer face 115. Flat face 115 of proximal ring 106 may facilitate connection of proximal ring 106 to sleeve 102. For example, flat face 115 can provide increased surface area by which proximal ring 106 can be attached to sleeve 102. In an example, flat face 115 provides an enlarged surface to heat seal proximal ring 106 to the distal end of sleeve 102.

Figure 1C:
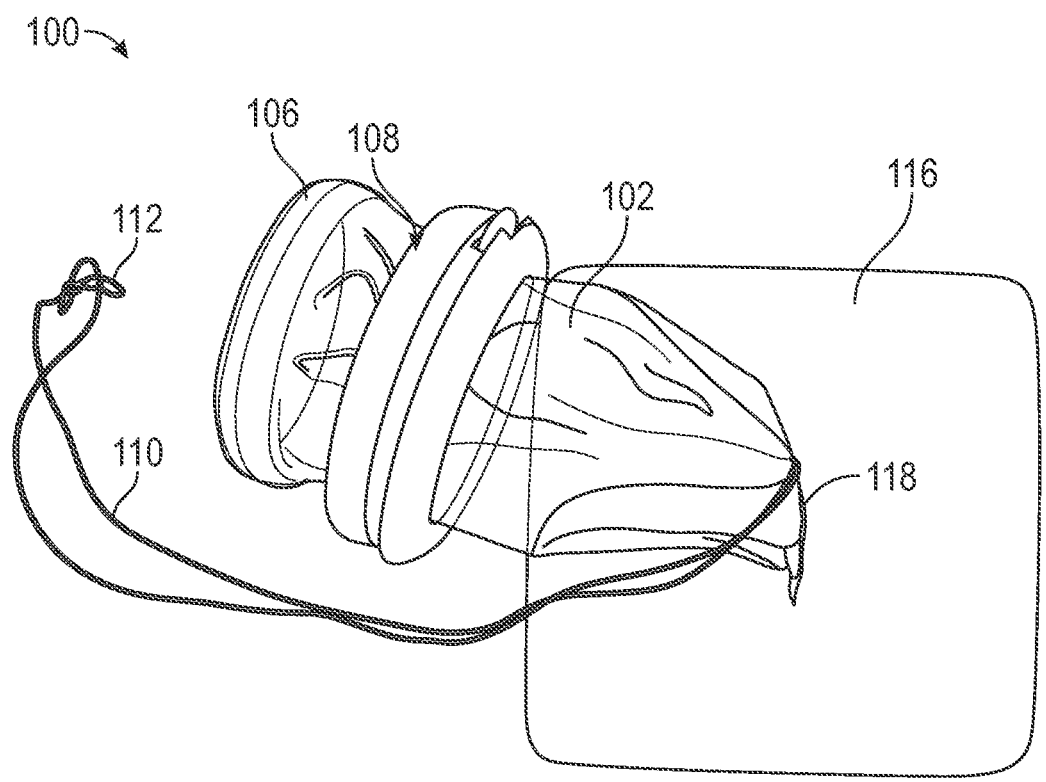
FIGS. 1C-1G depict the example wound retractor of FIG. 1A being inserted into and secured to retract an incision in a body wall.
Figure 1E:
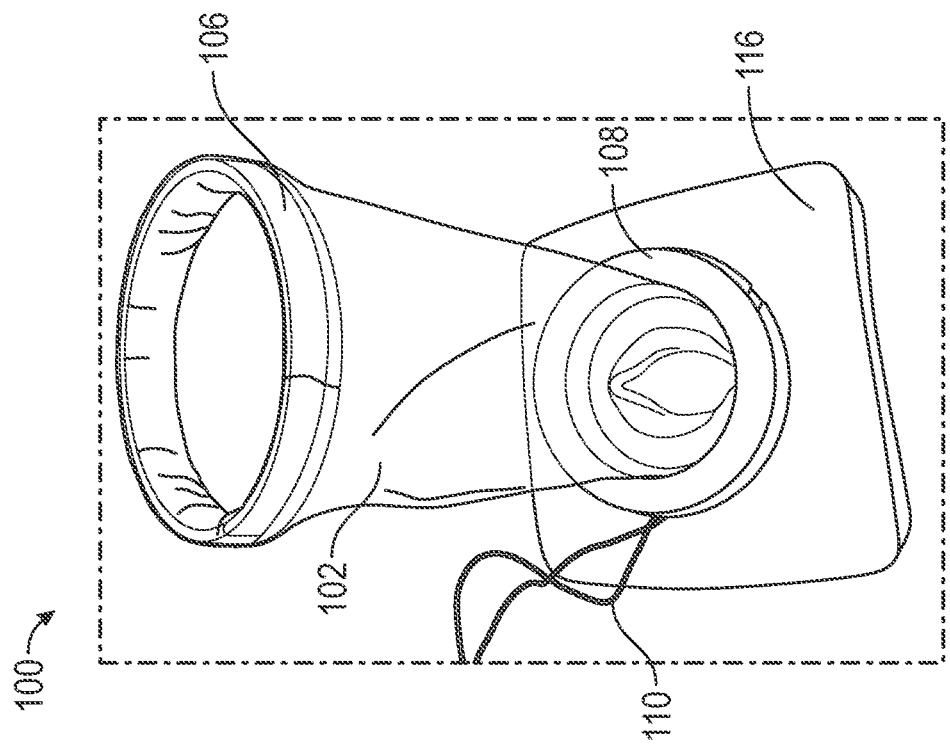
Figure 1D:
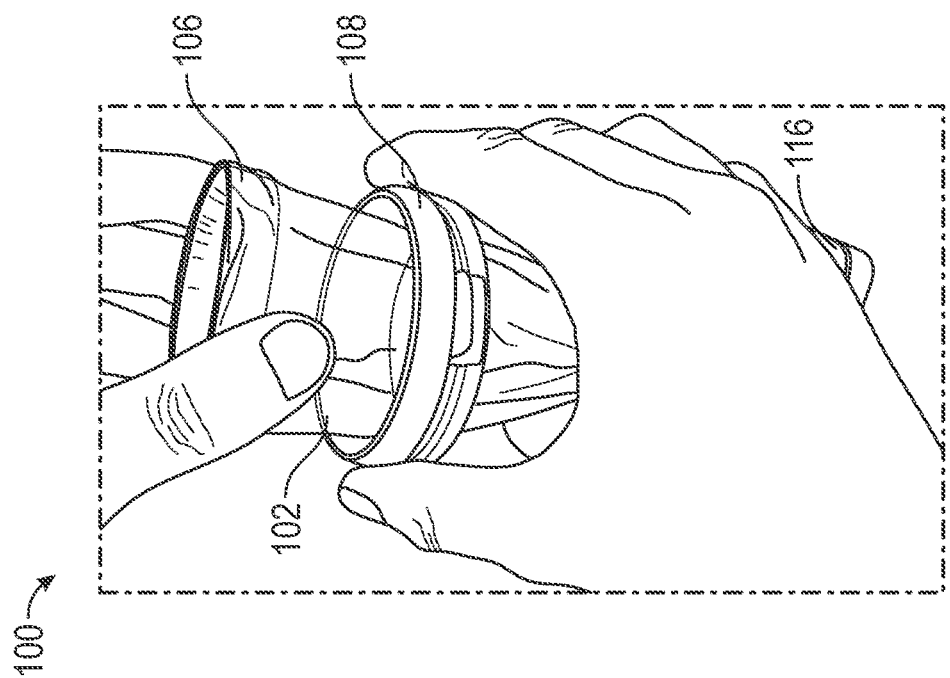

FIGS. 1C-1G depict example wound retractor 100 of FIG. 1A being inserted into and secured to retract an incision in a body wall. In FIG. 1C, body wall 116 includes incision 118. Distal ring 104 has been inserted through incision 118 and is therefore not visible in FIG. 1C. After distal ring 104 is inserted through incision 118, sleeve 102 can be pulled proximally away from the incision to pull distal ring 104 into contact with the inner surface of body wall 116 and to begin to place tension on sleeve 102. As depicted in FIG. 1D, for example, proximal ring 106 and/or collar 108 can be pulled on to pull/extend and tension sleeve 102. Additionally, auto-locking collar 108 can be slid distally along sleeve 102 by simply applying a proximal-to-distal force on collar 108, which is configured to slide freely in this direction toward the distally located body wall 116 and incision 118.

As depicted in FIGS. 1D and 1E, collar 108 can be slid down to engage the outer surface of body wall 116. Auto-locking collar 108 is configured to slide freely in the proximal-to-distal direction. A proximal-to-distal force can be applied to collar 108 to cause sleeve 102 to placed in tension between collar 108 and distal ring 104, which causes incision 118 to dilate. As collar 108 is pushed down and begins to place sleeve 102 in tension, the auto-locking shape, structure, and configuration of collar 108 automatically locks the position of collar 108 relative to sleeve 102 against movement in a distal-to-proximal direction, which functions to maintain the tension in sleeve 102 even after the external force is removed, for example, after the clinician stops pushing collar 108 down against body wall 116, as depicted in FIG. 1E.

Figure 1G:
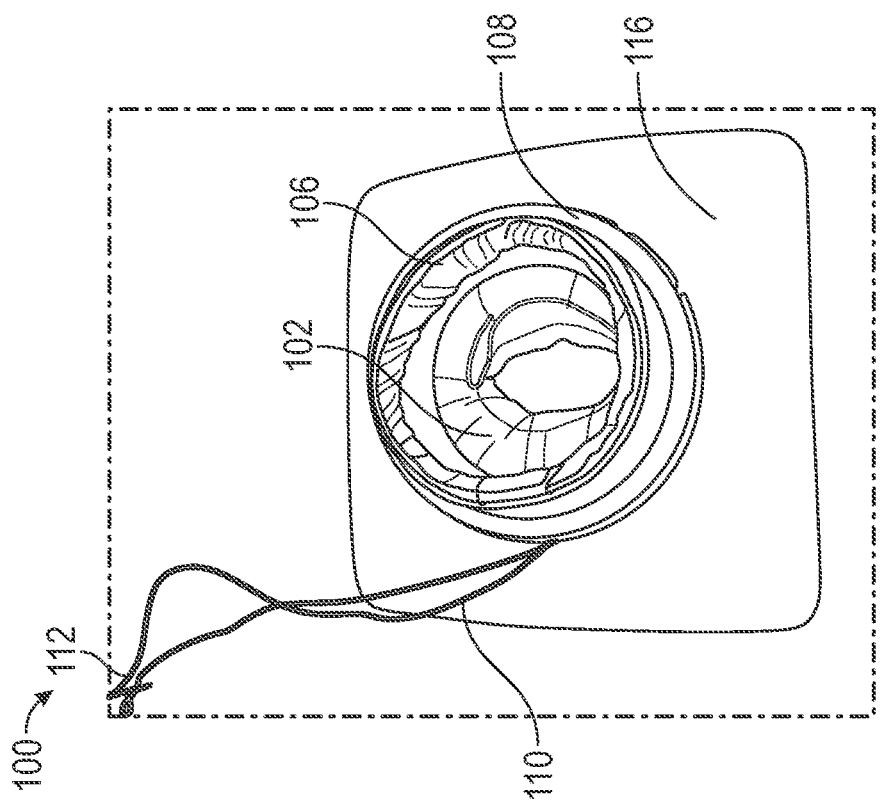
Figure 1F:
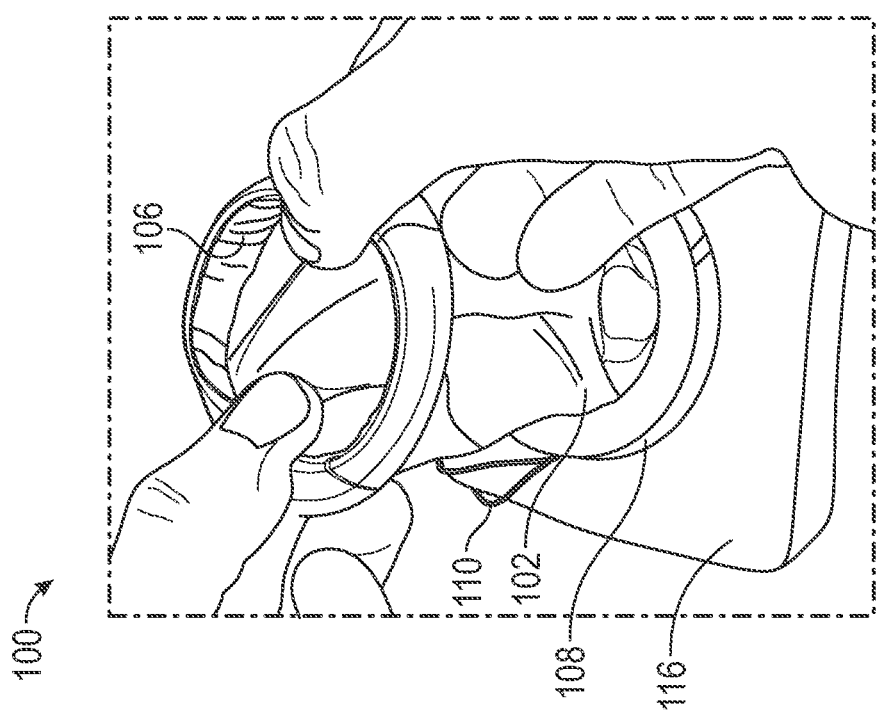

FIGS. 1F and 1G depict the adjustment (rolling up) of the length of sleeve 102 proximal of the incision and wound retractor 100 fully engaged with and dilating incision 118 in body wall 116. As FIGS. 1F and 1G illustrate, the proximal end of sleeve 102 can be wrapped around proximal ring 106 successively until the excess length of sleeve 102 between collar 108 and proximal ring 106 is fully rolled up around ring 106. After rolling up the excess length of sleeve 102, proximal ring 106 with sleeve 102 wrapped there around can be seated on a proximal side of collar 109, as depicted in FIG. 1G. After wound retractor 100 has been deployed in and is dilating incision 118, an access port device can be coupled to retractor 100 to establish and maintain insufflation pressure and to seal the surgical site against contaminants.

Figure 1H:
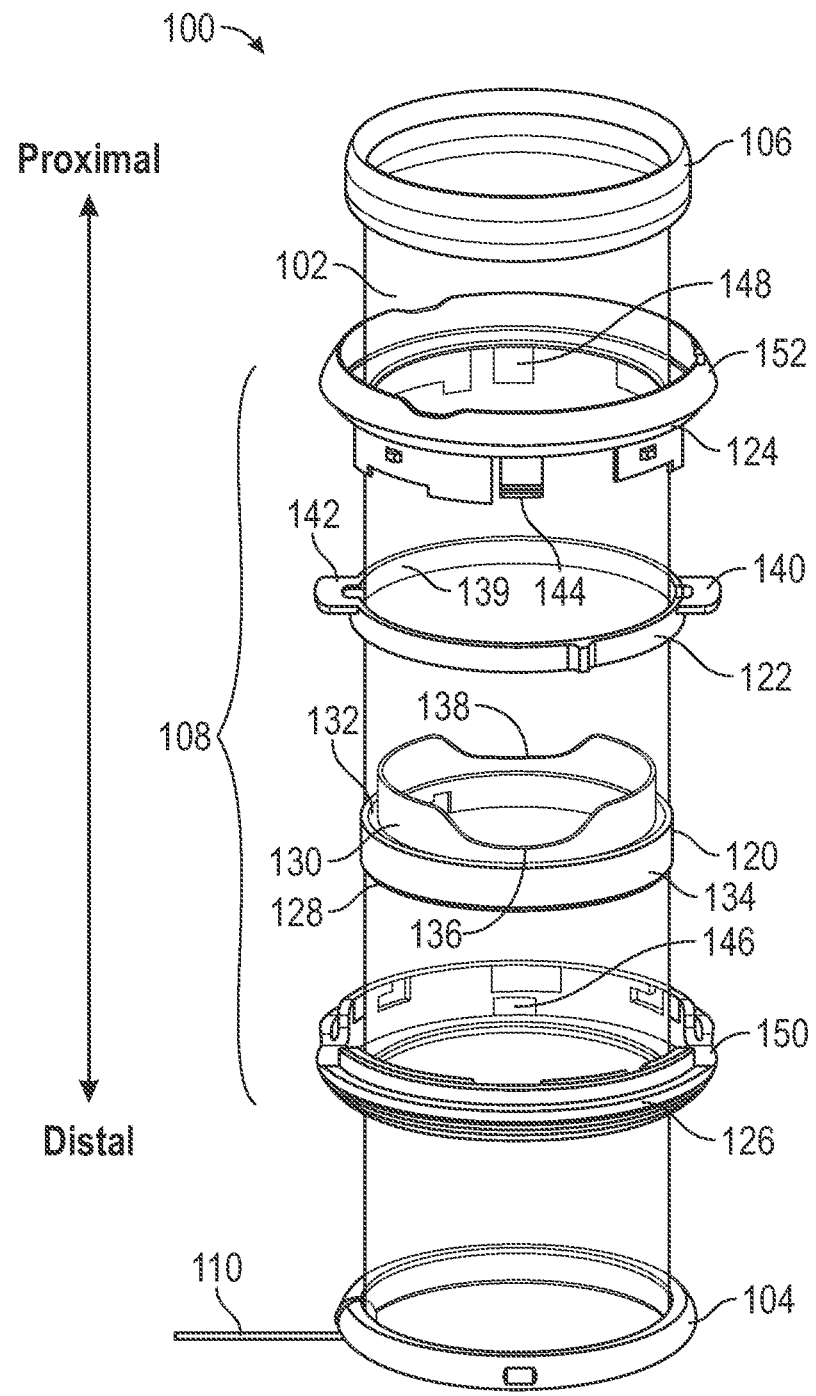
FIG. 1H is an exploded view depicting a wound retractor with an auto-locking collar.
Figure 1I:
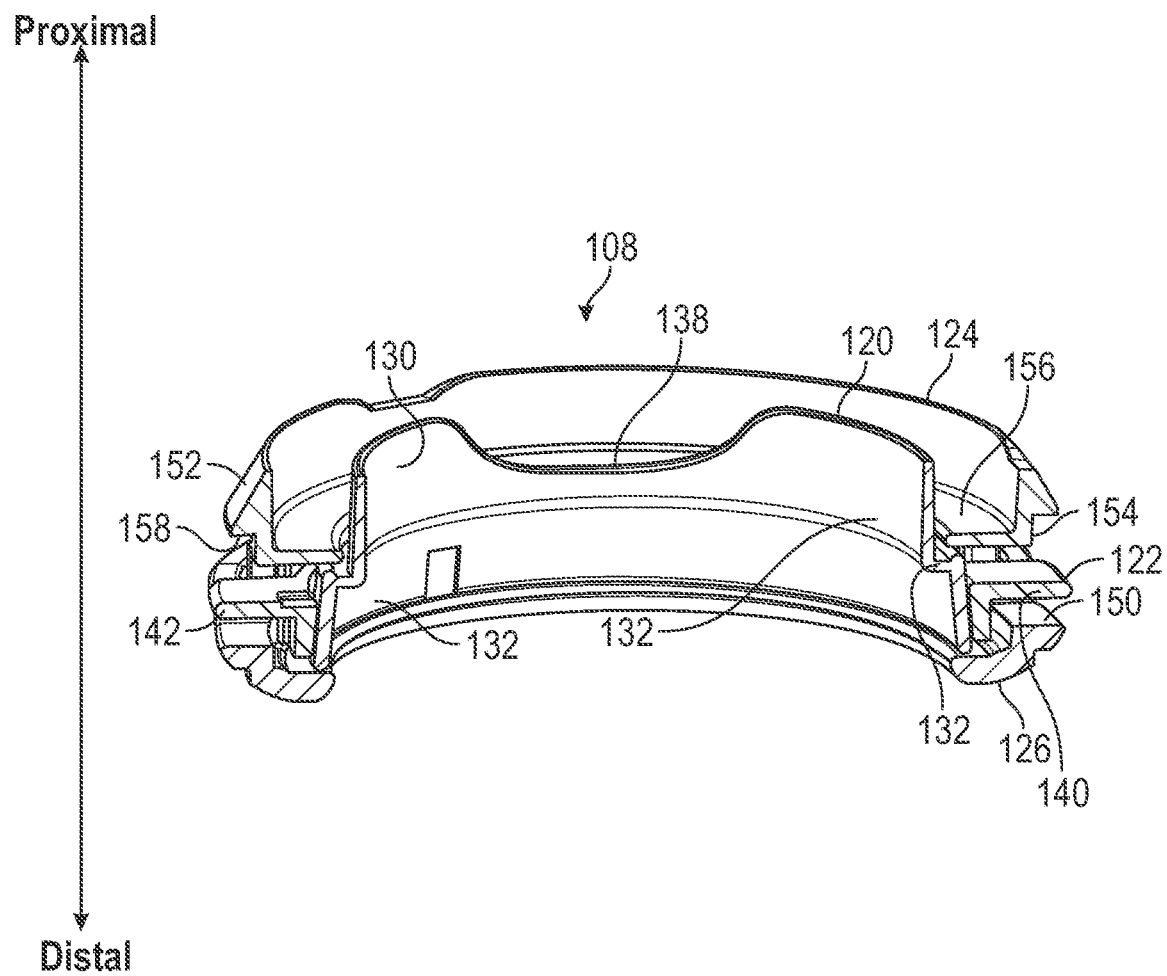
FIG. 1I is a section view of an auto-locking collar of a wound retractor in accordance with this disclosure.

FIG. 1H is an exploded view depicting wound retractor 100 with auto-locking collar 108. FIG. 1I is a section view of auto-locking collar 108. The section view of FIG. 1I does not show sleeve 102. However, the arrangement of sleeve 102 through locking collar 108 will be depicted in and described with reference to FIGS. 1J and 1K.

Referring to FIGS. 1H and 1I, collar 108 includes inner ring 120, outer ring 122, proximal housing section 124, and distal housing section 126. Inner ring 120 is inside and generally concentrically arranged with sleeve 102. Outer ring 122 is outside and generally concentrically arranged with sleeve 102. And, proximal and distal housing sections 124 and 126 are outside and generally concentrically arranged with sleeve 102. Proximal and distal housing sections 124 and 126 are configured to be removably coupled to one another to capture inner ring 120 and outer ring 122.

Inner ring 120 includes conical section 128 and cylindrical section 130. Cylindrical section 130 is proximal to conical section 128. Conical section 128 is joined to cylindrical section 130 by ledge 132. Ledge 132 extends radially inward from conical section 128 to join to cylindrical section 130. In examples, an outer diameter of cylindrical section 130 can be less than a minimum outer diameter of conical section 128. Conical section 128 includes tapered outer surface 134. Tapered outer surface 134 increases in diameter from a proximal end of inner ring 120 toward a distal end of inner ring 120. Cylindrical section 130 can include at least one circumferential notch 136. In examples, cylindrical section 130 includes first circumferential notch 136 and second circumferential notch 138. First circumferential notch 136 is disposed diametrically opposite second circumferential notch 138. Circumferential notches 136 and 138 can facilitate a clinician grasping and unrolling sleeve 102 from around proximal ring 104.

Outer ring 122 includes tapered inner surface 139 that increases in diameter from a proximal end of outer ring 122 toward a distal end of outer ring 122. A portion of sleeve 102 is captured between tapered outer surface 134 of inner ring 120 and tapered inner surface 139 of outer ring 122. Outer ring 122 also includes at least one unlock tab 140 extending radially outward from the outer ring. In examples, outer ring 122 includes first unlock tab 140 extending radially outward from outer ring 122 and second unlock tab 142 extending radially outward from outer ring 122. First unlock tab 140 is diametrically opposed to second unlock tab 142. Unlock tabs 140 and 142 (together or separately) are configured to unlock inner ring 120 and outer ring 122 from sleeve 102 in response to a force on the unlock tab(s) in a direction from the distal end of sleeve 102 toward the proximal end of sleeve 102 (or, more generally, in response to a force in a distal-to-proximal direction).

Inner ring 120 and outer ring 122 of collar 108 can be made from a variety of polymers. Inner ring 120 and outer ring 122 can be made from the same or different materials. In one example, inner ring 120 and outer ring 122 of collar 108 is made from a polycarbonate.

As noted above, collar 108 includes proximal housing section 124, and distal housing section 126. Proximal housing section 124 and distal housing section 126 are outside of and generally concentric with sleeve 102. Proximal housing section 124 and distal housing section 126 are configured to be removably coupled to one another to capture inner ring 120 and outer ring 122. Proximal housing section 124 includes at least one tab 144 configured to engage notch 146 in distal housing section 126 to removably couple the proximal housing section and the distal housing section to one another. In an example, proximal housing section 124 includes first tab 144 and second tab 146 configured to engage respective notches 146 (only one notch is visible in FIG. 1H) in distal housing section 126. Distal housing section 126 includes notches 150, which are configured to receive first tab 144 and second tab 146 of proximal housing section 124.

Referring to FIG. 1G, proximal housing section 124 includes tapered outer surface 152 that increases in diameter from a proximal end of proximal housing section 124 toward a distal end of proximal housing section 124. Proximal housing section 124 also includes cylindrical section 154 proximal to tapered outer surface 152. Proximal housing section 124 includes ledge 156 extending radially inward from cylindrical section 152. Ledge 156 and the inner surface of cylindrical section 132 of inner ring 120 and the outer surface of cylindrical section 130 of inner ring 120 combine to form a circumferential channel within which sleeve 102 rolled up around proximal ring 106 can rest. And, proximal housing section 124 includes lip 158 extending radially inward from a distal end of tapered outer surface 152 to cylindrical section 154. As described in more detail with reference to FIGS. 3E-3G, lip 158 can act as catch for a clamp that is configured to be coupled to wound retractor 100.

Figure 1J:
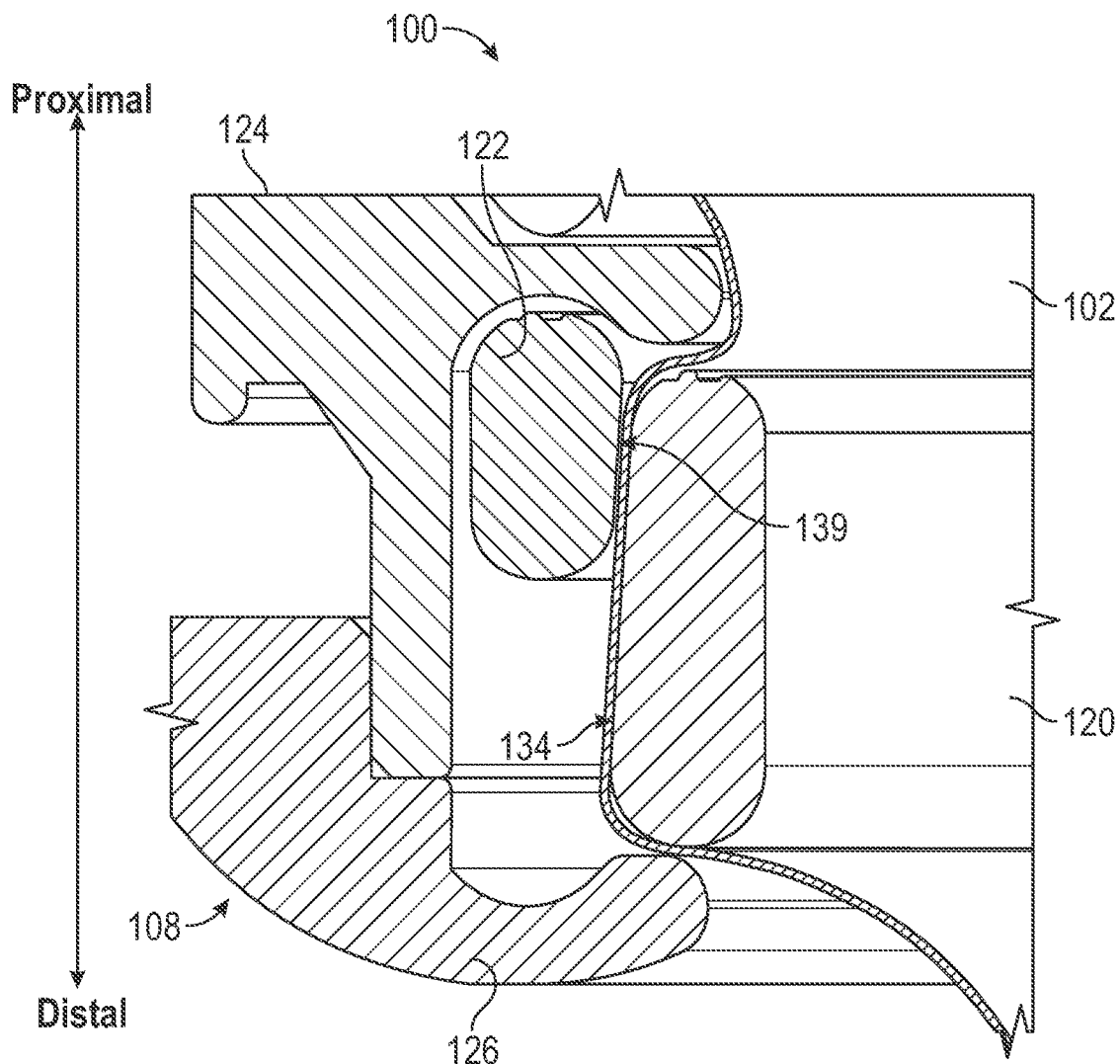
FIG. 1J depicts an outer ring of an auto-locking collar in an unlocked position.
Figure 1K:
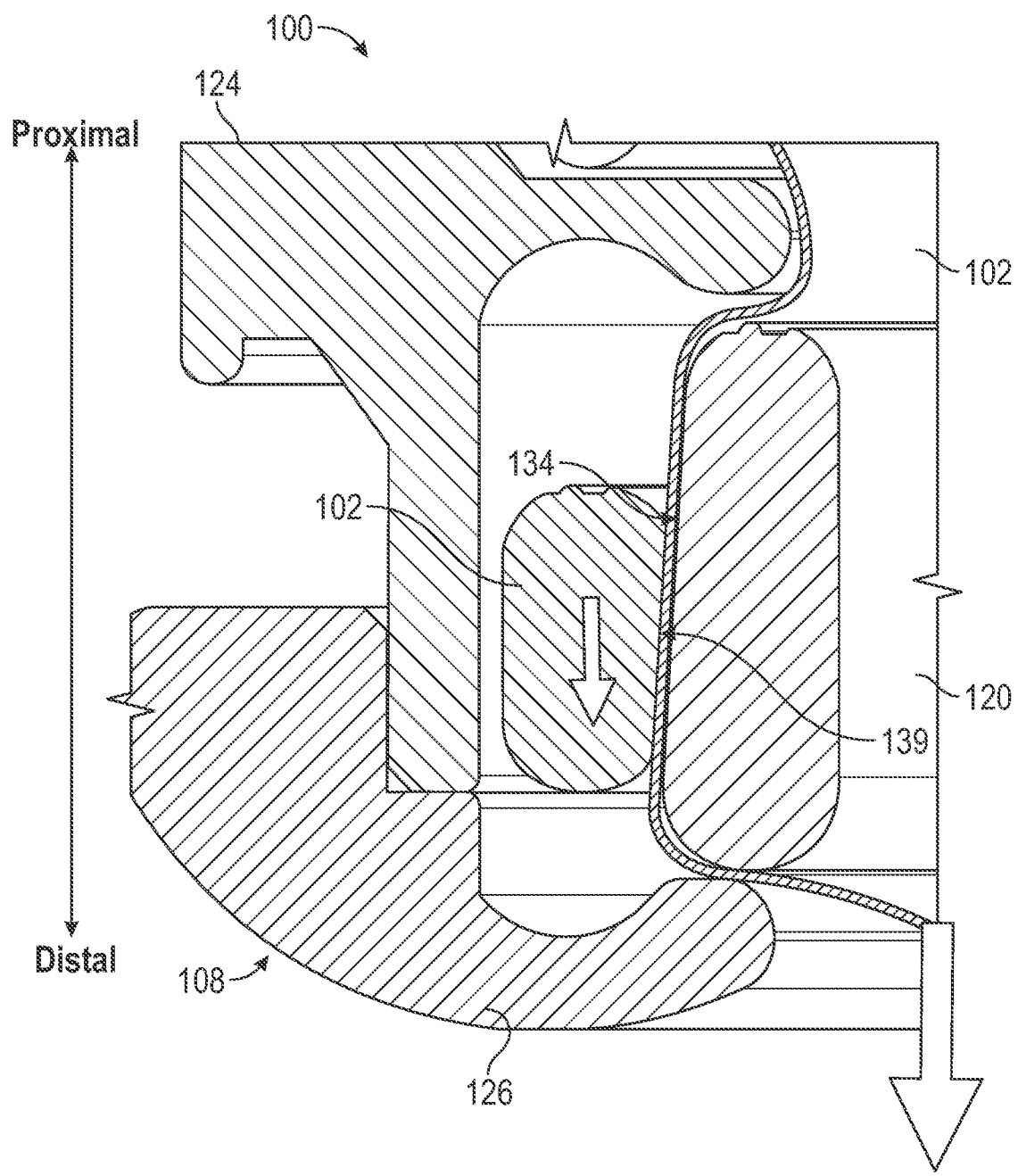
FIG. 1K depicts an outer ring of an auto-locking collar in a locked position.

FIGS. 1J and 1K are section views depicting wound retractor 100 with auto-locking collar 108. FIG. 1J depicts outer ring 122 of collar 108 in an unlocked position and FIG. 1K depicts outer ring 122 in a locked position. In FIGS. 1J and 1K, proximal housing section 124 and distal housing section 126 are coupled to one another to capture inner ring 120 and outer ring 122. Additionally, sleeve 102 is fed through auto-locking collar 108 between tapered outer surface 134 of inner ring 120 and tapered inner surface 139 of outer ring 122. Inner ring 120 and inner ring 122 can be in clearance with proximal and distal housing sections 124 and 126, but can also be captured by the housing so that the entire auto-locking collar 108 moves together along sleeve 102.

In FIG. 1J, outer ring 122 of collar 108 in an unlocked position in which outer ring 122 is in a relative proximal position within proximal housing section 124. A portion of sleeve 102 is between tapered outer surface 134 of inner ring 120 and tapered inner surface 139 of outer ring 122. In the proximal unlocked position of outer ring 122 there is a relatively small clearance between tapered inner surface 139 of outer ring 122 and sleeve 102 and between sleeve 102 and tapered outer surface 134 of inner ring 120. In the configuration of collar 108 depicted in FIG. 1J, in which outer ring 122 is in the proximal unlocked position, sleeve 102 will move relatively freely from any mechanical interference (e.g., from tapered inner surface 139 and tapered outer surface 134) through collar 108 when the collar is moved/slid in a proximal-to-distal direction. Additionally, to the extent sleeve 102, tapered inner surface 139, and tapered outer surface 134 exert any forces on one another (e.g., friction), any resultant tensioning of sleeve 102 or friction between sleeve 102 and tapered inner surface 139 will be in a distal-to-proximal direction, which will tend to cause outer ring 122 to move proximally and therefore will maintain outer ring 122 in the proximal unlocked position.

However, as auto-locking collar 108 is moved/slid proximally along sleeve 102 and engages the body wall of the patient, the resultant tensioning in sleeve 102 will be in a proximal-to-distal direction and will cause outer ring 122 to move distally within proximal housing section 124 to the distal locked position depicted in FIG. 1K. As outer ring 122 moves/slides from the proximal unlocked position depicted in FIG. 1J to the distal locked position depicted in FIG. 1K, tapered inner surface 139 of outer ring 122 is pressed against sleeve 102 and tapered outer surface 134 of inner ring 120 to form a taper lock with sleeve 102 locked against movement relative to collar 108.

In examples, tapered inner surface 139 of outer ring 122 and tapered outer surface 134 of inner ring 120 have the same surface slope/angle and are thereby sized and shaped to match one another on either side of sleeve 102. In other examples, however, tapered inner surface 139 of outer ring 122 and tapered outer surface 134 of inner ring 120 may have different surface slopes/angles, which may function to We modulate the relative ease (or difficulty) with which auto-locking collar 108 can be slid along sleeve 102.

Outer ring 122 includes first unlock tab 140 and second unlock tab 142 extending radially outward from outer ring 122 (see FIGS. 1H and 1I). Unlock tabs 140 and 142 (together or separately) are configured to unlock inner ring 120 and outer ring 122 from sleeve 102 in response to a force on the unlock tab(s) in a distal-to-proximal direction. Thus, after auto-locking collar 108 is slid down to engage the body wall and tension sleeve 102 and outer ring 122 moves into to the distal locked position depicted in FIG. 1K, a clinician can adjust wound retractor 100 by exerting force on unlock tabs 140 and 142 in a distal-to-proximal direction to unlock inner and outer rings 120 and 122 and release auto-locking collar 108 to slide proximally along sleeve 102.

Wound retractor 100 (and other wound retractors in accordance with this disclosure) creates a channel through the body wall of the patient and may not include structures for maintaining insufflation pressure or sealing the surgical site against contaminants. As such, wound retractor 100 can be made to be coupled to various types of instrument access port devices to establish and maintain insufflation pressure and to seal the surgical site against contaminants. For example, wound retractor 100 can be coupled to an access port device with a sealed port for receiving a manually operated or teleoperated surgical instrument.

Additionally, wound retractor 100 can be coupled to an access port device that is configured to receive and seal multiple teleoperated and/or manually operated surgical instruments through the one access port device coupled to a wound retractor for a single surgical site. In such cases, the access port device may employ an instrument entry guide, which includes a cannula received in a port of the access port device. The entry guide and cannula can include multiple sealed instrument channels so that a single cannula (in some cases, including multiple lumens) and port can be employed to receive multiple surgical instruments.

Figure 2:
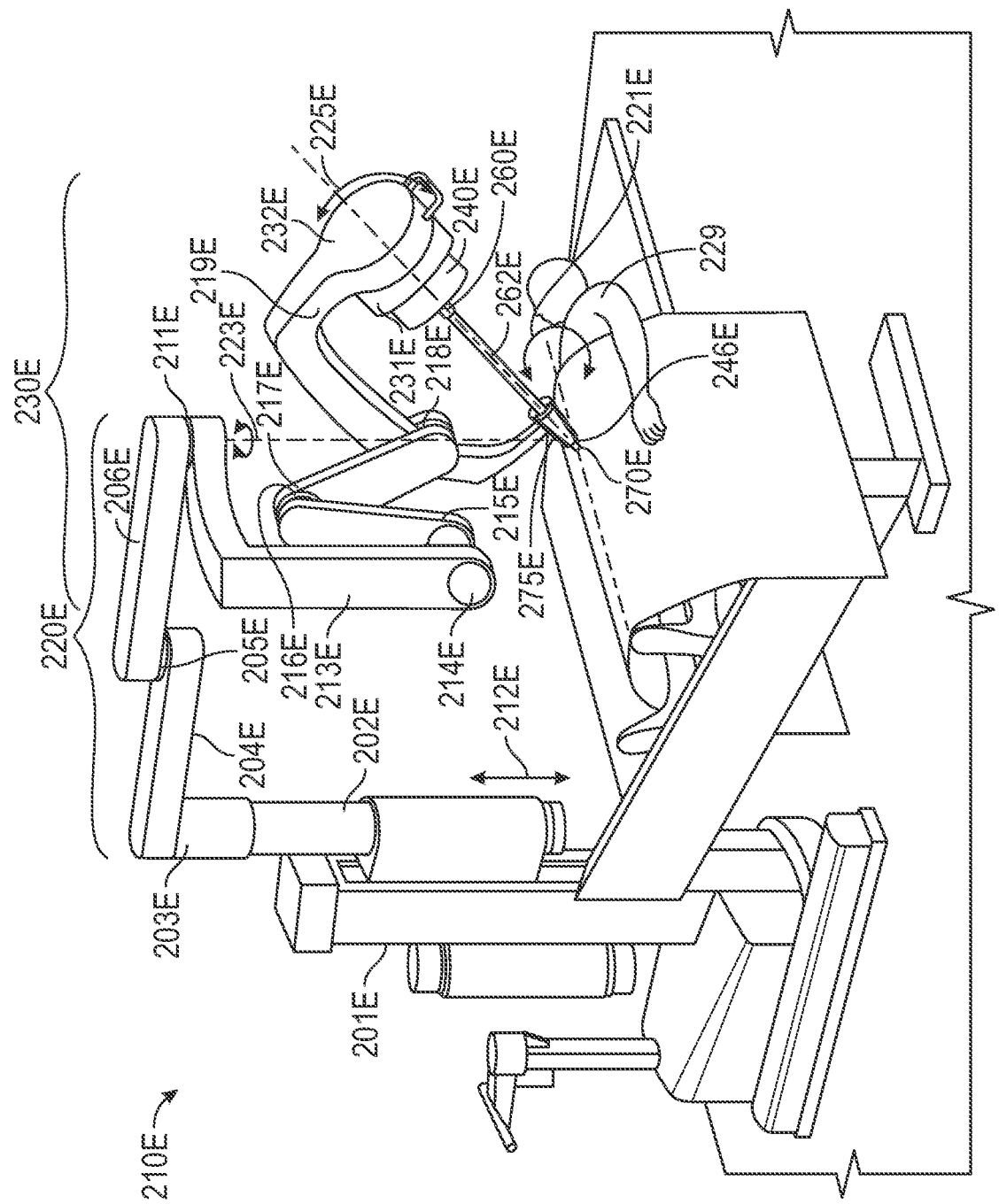
FIG. 2 is a schematic perspective view depicting aspects of an example telesurgical system.

To illustrate the general context in which a wound retractor as described above may be used, FIG. 2 provides a schematic perspective view that illustrates aspects of a telesurgical system in accordance with various embodiments. The telesurgical system of FIG. 2 is configured to deliver multiple surgical instruments through a single surgical site (e.g., incision) and using an access port device coupled to a wound retractor in accordance with this disclosure and with a multiple instrument entry guide coupled to the access port device.

In general, for the purposes of this description, a telesurgical system includes three main components: an endoscopic imaging system, a user control system (master), and a manipulator system 210E (slave) (shown in FIG. 2), all interconnected by wired (electrical or optical) or wireless connections. One or more data processors (i.e., one or more logical units coupled to one or more memory systems) may be variously located in these main components to provide system functionality. Examples are disclosed in U.S. Pat. No. 9,060,678 (filed Jun. 13, 2007) (disclosing "Minimally Invasive Surgical System"), which is incorporated by reference herein.

The imaging system performs image processing functions on, e.g., captured endoscopic imaging data of the surgical site and/or preoperative or real-time image data from other imaging systems external to the patient. The imaging system outputs processed image data (e.g., images of the surgical site, as well as relevant control and patient information) to a surgeon at user control system. In some aspects, the processed image data is output to an optional external monitor visible to other operating room personnel or to one or more locations remote from the operating room (e.g., a surgeon at another location may monitor the video; live feed video may be used for training; etc.).

The user control system includes multiple-degrees-of-freedom mechanical input devices that allow the surgeon to manipulate the instruments, entry guide(s), and imaging system devices, with computer assistance. These input devices may in some aspects provide haptic feedback from the instruments and surgical device assembly components to the surgeon. The user control system also includes a stereoscopic video output display positioned such that images on the display are generally focused at a distance that corresponds to the surgeon's hands working behind/below the display screen.

Control during insertion and use of the instruments may be accomplished, for example, by the surgeon moving the instruments presented in the image with one or two of the input devices; the surgeon uses the input devices to translate and rotate the instrument in three-dimensional space. Similarly, one or more input devices may be used to translate and rotate the imaging system or an associated surgical device assembly to steer an endoscope or instrument cluster towards a desired location on the output display and to advance inside the patient.

A manipulator system 210E is illustrated in FIG. 2. In the depicted example, the manipulator system 210E is implemented as a patient-side cart, and the surgery is in the abdomen of patient 229. However, the surgical system including manipulator system 210E can be used for a wide variety of surgeries by using various combinations of instruments.

Manipulator system 210E includes a floor-mounted base 201E as shown, or alternately a ceiling-mounted or other mechanically grounded base (not shown). Base 201E may be movable or fixed (e.g., to the floor, ceiling, wall, or other equipment such as an operating table). Base 201E supports the remainder of the manipulator system, which includes a usually passive, uncontrolled manipulator support structure 220E and an actively controlled manipulator system 230E, herein also referred to as entry guide manipulator 230E.

In one example, the manipulator support structure 220E includes a first setup link 202E and two passive rotational setup joints 203E and 205E. Rotational setup joints 203E and 205E allow manual positioning of the coupled setup links 204E and 206E. Alternatively, some of these setup joints may be actively controlled, and more or fewer setup joints may be used in various configurations. Setup joints 203E and 205E and setup links 204E and 206E allow a person to place entry guide manipulator 230E at various positions and orientations in Cartesian x, y, z space. A passive prismatic setup joint (not shown) between link 202E of manipulator support structure 220E and base 201E may be used for large vertical adjustments 212E.

Entry guide manipulator 230E includes an entry guide manipulator assembly 231E that supports a plurality of surgical device assemblies, at least one surgical device assembly being coupled to entry guide manipulator assembly 231E during a surgery. Each surgical device assembly includes a teleoperated manipulator and either a surgical instrument or a camera instrument mounted on the manipulator. For example, in FIG. 2, one surgical device assembly includes, mounted to manipulator 240E, an instrument 260E with a shaft 262E that extends through one of typically multiple channels of entry guide 270E during a surgical procedure.

The procedure conducted on the patient is carried out through a surgical site with an incision near entry guide 270E in the example of FIG. 2. In examples according to this disclosure, the incision in the body wall of the patient can be prepared and dilated by an auto-locking wound retractor, for example, retractor 100 in accordance with this disclosure. The auto-locking wound retractor can be connected to an access port device that is configured to receive and seal a cannula of entry guide 270E.

Entry guide manipulator assembly 231E includes an instrument manipulator positioning system (hereinafter simply "positioning system"). The positioning system moves instrument mount interfaces of one or more manipulators 240E in a plane so that, when one or more instruments 260E are coupled to entry guide manipulator assembly 231E using the respective instrument mount interfaces, the shafts of the instruments 260E are each aligned for insertion into one of the channels in entry guide 270E. While the entry guide 270E is depicted as located at a body wall of the patient, it is to be understood that the manipulator system 210E can also be used, without need for modifications, with entry guides located at a distance from the body wall in an entry guide receptacle of an instrument access device as herein described.

The instrument mount interface(s) may be moved into position after attachment of the instrument(s). The plane in which the instrument mount interfaces are moved is generally perpendicular to the lengthwise axis of entry guide 270E, and the trajectories that instrument mount interfaces take in that plane may include straight and/or curved portions in various combinations. As a positioning element of a lateral motion mechanism of the positioning system moves along a trajectory, the instrument mount interface, and effectively a distal tip of a shaft of an instrument coupled to the instrument mount interface, moves along the same trajectory. Thus, motion of the positioning element causes the shaft to be moved to a location where the shaft is aligned with a channel in entry guide 270E. In this position, the shaft can enter and pass through the channel in entry guide 270E without damaging the instrument and without inhibiting operation of the instrument. The particular paths implemented in the positioning system depend at least in part on the types of surgical device assemblies that can be mounted on the entry guide manipulator assembly 231E and/or the configuration of channels in entry guide 270E.

Different entry guides may be used in different surgical procedures. An entry guide that enters the body between the ribs may optionally have a different shape than an entry guide that enters the body through an incision in the abdomen. Further, entry guides that enter the body generally differ, e.g., in length, from entry guides used outside the body, such as entry guides inserted through an entry guide receptacle at a proximal end of an envelope of an instrument access device as disclosed herein; entry guides used outside of and at a distance from the body may be shortened relative to those entering the body. The different shapes of the entry guides require different layouts of the channels that extend through the entry guides, i.e., different channel configurations. Also, the shapes and/or sizes of the shafts of the instruments may be different for different instruments. An entry guide is used that accommodates the shapes and sizes of the shafts of the instruments used in a particular surgical procedure. The trajectories are designed to accommodate a set of entry guides that can be used with manipulator system 210E.

The ability to individually position an instrument, and hence its shaft, with respect to a channel in an entry guide by moving an instrument mount interface provides versatility to manipulator system 210E. For example, this ability allows entry guides with different channel configurations to be used in system 210E. In addition, the positioning system eliminates the need for surgical-procedure-specific instruments. In other words, the instrument manipulator positioning system allows use of a common set of instruments with a variety of entry guides by moving the instrument shafts around, as described above.

Entry guide manipulator 230E includes a kinematic chain of active joints and links that are movable by motors or other actuators and receive movement control signals that are associated with master arm movements at the user control system. Using this kinematic chain, the entry guide manipulator 230E can adjust the position and orientation of the positioning system of entry guide manipulator assembly 231E and, by extension, the instrument. Usually, the entry guide manipulator 230E is configured and operated to constrain rotation of an instrument at a point located on the instrument's shaft, herein referred to as a remote center of motion.

Conventionally, the remote center of motion coincides generally with the position at which an instrument enters the patient (e.g., at the umbilicus for abdominal surgery). In accordance with this disclosure, however, where an instrument access device with an instrument entry guide located outside the body (in a port at the proximal end of the envelope of the instrument access device) is used, the position of the remote center of motion likewise falls outside the body, e.g., slightly above the body wall, and generally along the axis of the entry guide. A remote center of motion above the body wall allows for instruments to be moved radially outward from the entry guide's extended axis proximally of the patient's body wall and so get better triangulation access at or in the incision. Flexible instrument shafts in conjunction with a flexible wound retractor render such flexibility in operating the instruments possible without risking trauma to tissue.

The remote center of motion is the location at which yaw, pitch, and roll axes intersect, i.e., the location at which the kinematic chain of entry guide manipulator 230E remains effectively stationary while joints move through their range of motion. As shown in FIG. 2, a manipulator assembly yaw joint 211E is coupled between an end of setup link 206E and a first end, e.g., a proximal end, of a first manipulator link 213E. Yaw joint 211E allows first manipulator link 213E to move with reference to link 206E in a motion that may be arbitrarily defined as "yaw" around a manipulator assembly yaw axis 223E. As shown, yaw axis 223E of joint 211E is aligned with a remote center of motion located at or near the entry guide 270E.

A distal end of first manipulator link 213E is coupled to a proximal end of a second manipulator link 215E by a first actively controlled rotational joint 214E. A distal end of second manipulator link 215E is coupled to a proximal end of a third manipulator link 217E by a second actively controlled rotational joint 216E. A distal end of third manipulator link 217E is coupled to a fourth manipulator link 219E by a third actively controlled rotational joint 218E; the fourth manipulator link 219E extends in both directions away from the rotational joint 218E and, thus, has two distal ends relative to the location of the joint 218E.

In one embodiment, links 215E, 217E, and 219E are coupled together to act as a coupled motion mechanism. Coupled motion mechanisms are well known (e.g., such mechanisms are known as parallel motion linkages when input and output link motions are kept parallel to each other). For example, if rotational joint 214E is actively rotated, then joints 216E and 218E are also actively rotated so that link 219E moves with a constant relationship to link 215E. Therefore, it can be seen that the rotational axes of joints 214E, 216E, and 218E are parallel. When these axes are perpendicular to yaw axis 223E of joint 211E, links 215E, 217E, and 219E move with reference to link 213E in a motion that may be arbitrarily defined as "pitch" around a manipulator assembly pitch axis. The manipulator pitch axis extends into and out of the page in FIG. 2 at remote center of motion at or near the entry guide 270E. The motion around the manipulator assembly pitch axis is represented by arrow 221E. Since links 215E, 217E, and 219E move as a single assembly in this embodiment, first manipulator link 213E may be considered an active proximal manipulator link, and second through fourth manipulator links 215E, 217E, and 219E may be considered collectively an active distal manipulator link.

An entry guide manipulator assembly platform 232E is coupled to one of the distal ends of fourth manipulator link 219E. Entry guide manipulator assembly 231 is rotatably mounted on platform 232E. Entry guide manipulator assembly 231 can rotate a plurality of surgical device assemblies (e.g., 260E) as a group around axis 225E. Specifically, entry guide manipulator assembly 231 rotates as a single unit with reference to platform 232E in a motion that may be arbitrarily defined as "roll" around an entry guide manipulator assembly roll axis 225E.

In accordance with the present disclosure, all the instruments (including a camera instrument) enter the instrument access device via a single port, which is generally stationary relative to the remote center of motion imposed by entry guide manipulator 230E (and defined by the intersection of manipulator assembly yaw axis 223E, manipulator assembly pitch axis 221E, and manipulator roll axis 225E). The configuration of links 215E, 217E, and 219E, and the configuration of joints 214E, 216E, and 218E are such that remote center of motion is located distal of entry guide manipulator assembly, with sufficient distance to allow entry guide manipulator assembly to move freely with respect to the entry guide.

An entry guide receptacle 275E may be removably coupled (directly or indirectly via a mount) to the distal end of fourth manipulator link 219E opposite the distal end to which entry guide manipulator assembly platform 232E is coupled. In one implementation, the entry guide receptacle 275E or mount is coupled to link 219E by a rotational joint that allows it to move between a stowed position adjacent link 219E and an operational position that ensures that the remote center of motion is located along the entry guide receptacle 275E or the entry guide 270E received therein. During operation, the entry guide receptacle 275E is fixed in position relative to link 219E according to one aspect. Entry guide receptacles and entry guides may be made of various materials, e.g., steel or extruded plastic. Plastic, which is less expensive than steel, may be suitable for one-time use per surgical procedure.

The various passive setup joints/links and active joints/links allow positioning of the instruments and imaging system with a large range of motion when a patient 229 is placed in various positions on a movable table. Certain setup and active joints and links in the manipulator support structure 210E and/or entry guide manipulator 230E may be omitted to reduce the surgical system's size and shape, or joints and links may be added to increase degrees of freedom. It should be understood that the manipulator support structure 210E and entry guide manipulator 230E may include various combinations of links, passive joints, and active joints (redundant degrees of freedom may be provided) to achieve a necessary range of poses for surgery.

Figure 3A:
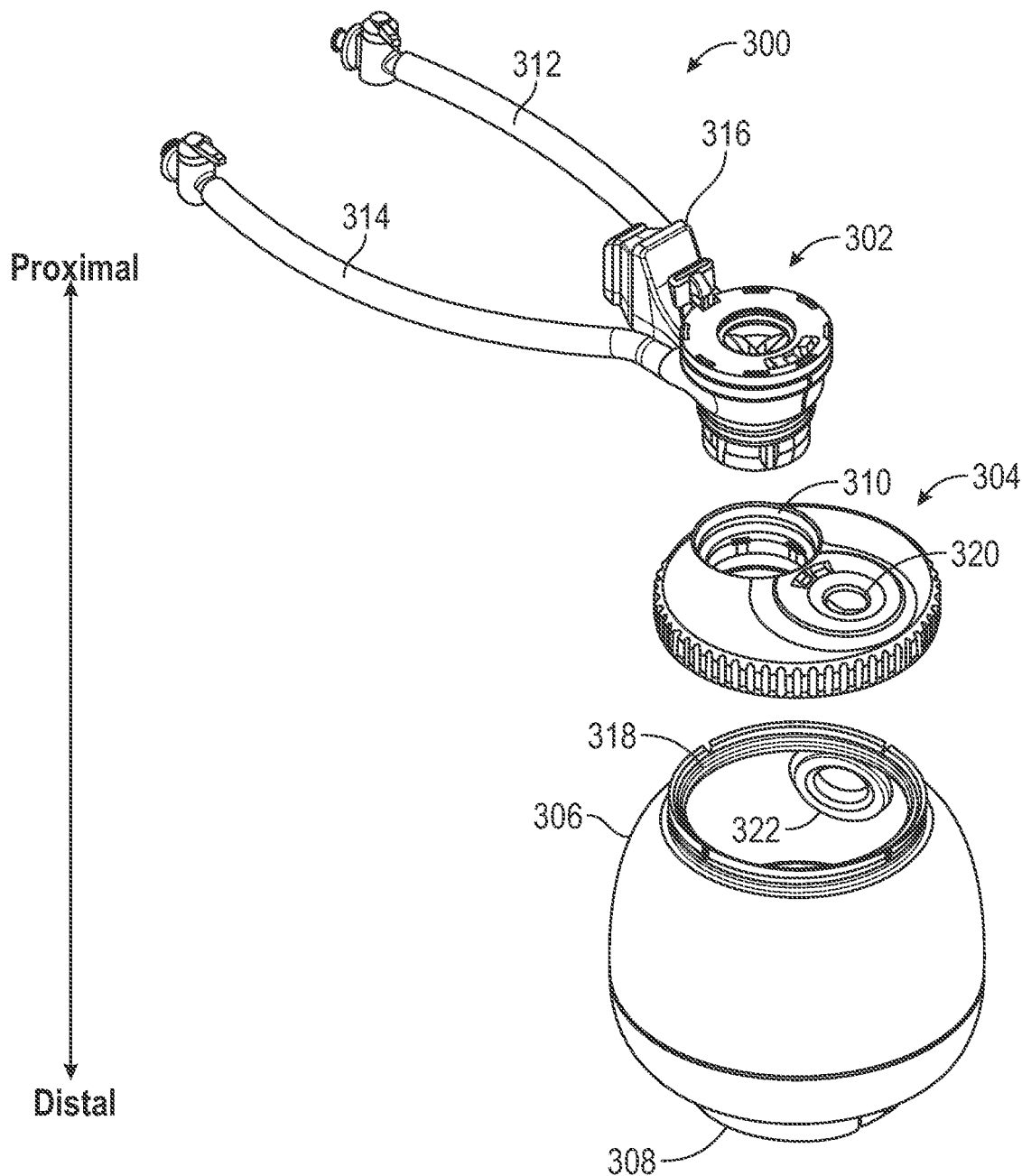
FIG. 3A depicts example instrument access device 300 coupled to a wound retractor in accordance with this disclosure.

FIG. 3A depicts example instrument access device 300 coupled to a wound retractor in accordance with this disclosure. An access port device coupled to a wound retractor commonly arranges the surgical instrument port of the access port device adjacent the incision and wound retractor. In such cases, articulation of the instruments of the teleoperated system commonly occurs just outside and above the incision site and the instrument end effectors are located inside the body below the incision and the outer surface of the body. Thus, in such situations, the end effectors that are manipulated by the surgeon in these types of procedures are located relatively deeply within the body of the patient.

There are situations, however, where it may be necessary or advantageous to control the end effectors of the instruments at or very close to the surface of the body at the incision site. In such situations, the challenge is maintaining insufflation of the body cavity of the patient while also providing enough room for the arms of the instruments to articulate outside the body such that the instrument end effectors are located at or near the surface of the body. FIG. 3A depicts an example multi-instrument single access port device 300, which is configured to receive and seal multiple teleoperated instruments through a single access port that receives a multi-instrument entry guide. Access port device 300 includes a pressurized and sealed envelope, which provides an operating space for arms/shafts of multiple instruments of a teleoperated surgical system to articulate outside the body such that instrument end effectors are located at or near the surface of the body at the incision site of the wound retractor coupled to the instrument access device.

In FIG. 3A, instrument access device 300 includes cannula assembly 302, instrument seal assembly 304, envelope 306, and clamp 308. Although it is not visible in FIG. 3A (see FIG. 3B), clamp 308 is coupled to an auto-locking wound retractor in accordance with disclosure. Cannula assembly 302 is received in cannula port 310 of instrument seal assembly 304. Additionally, cannula assembly 302 includes insufflation lines 312 and 314, which are configured to carry insufflation gas through the lines and into instrument access device 300, including into envelope 306. Cannula assembly 302 also includes blade 316. Blade 316 affixes instrument access device 300 to an arm of a teleoperated surgical system, such as the system depicted and described with reference to FIG. 2.

Instrument seal assembly 304 is connected to proximal opening 318 of envelope 306. Additionally, instrument seal assembly 304 includes assistant ports 320 and 322, which are configured to receive a manually operated instrument. Clamp 308 is connected to a distal opening of envelope 306 and removably connected to a wound retractor in accordance with this disclosure.

Figure 3B:
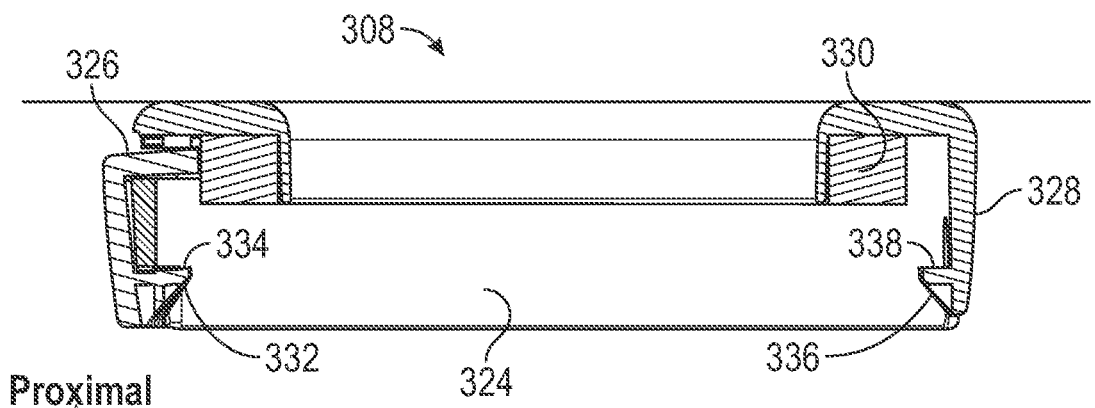
FIGS. 3B-3D depict an example wound retractor clamp in accordance with this disclosure.
Figure 3C:
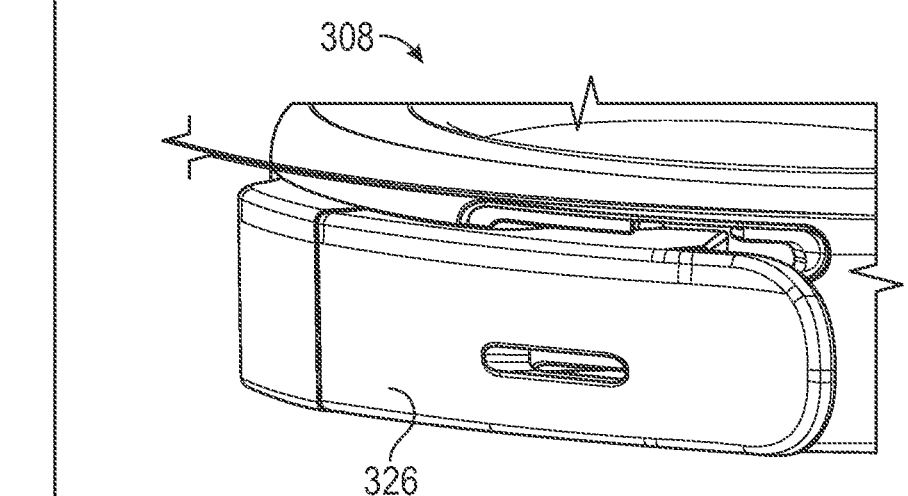
Figure 3D:
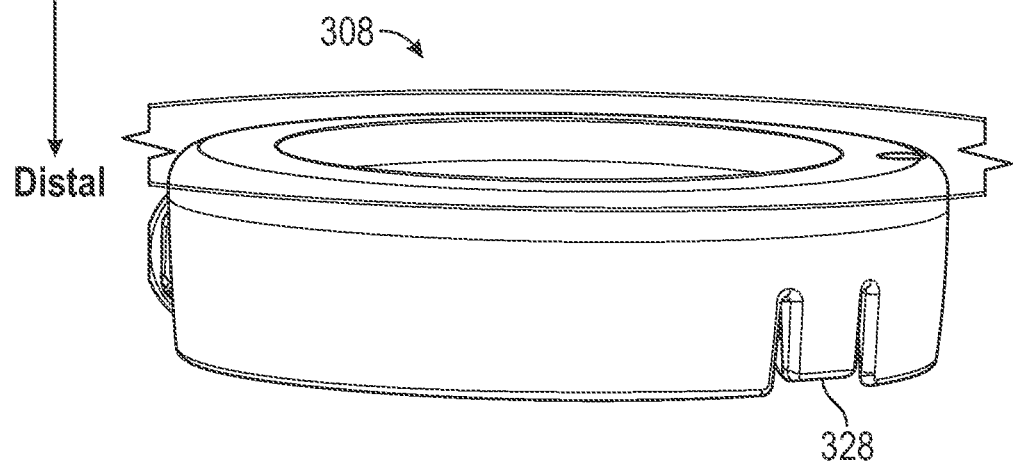

FIGS. 3B-3D depict example clamp 308 in accordance with this disclosure. Clamp 308 is configured to quickly and easily connect to and disconnect from example auto-locking wound retractors in accordance with this disclosure. Although clamp 308 is depicted (in FIGS. 3A and 3E) connected to multi-instrument single access port device 300, in other examples, clamp 308 (and other clamps in accordance with this disclosure) can be connected to a single port-single instrument access device or a multi-port access device.

In FIGS. 3B-3D, clamp 308 includes clamp body 324, lever 326, tab 328, and gasket 330. Lever 326 includes tapered surface 332 and lip 334 and tab 328 includes tapered surface 336 and lip 338. Tapered surface 332 of lever 326 and tapered surface 336 of tab 328 each increase in diameter from a distal end of clamp 308 toward a proximal end of the clamp. And, as will be described in detail with reference to FIG. 3E, lip 334 of lever 326 and lip 338 of tab 328 are configured to act as a catch (mechanical stop) to secure clamp 308 on a wound retractor in accordance with this disclosure. Clamp 308 is configured to be snapped onto a wound retractor in accordance with this disclosure and to be removed from the wound retractor by actuating lever to disengage one side of clamp 308 from the wound retractor and then tilting (pivoting) the lever side of clamp 308 proximally to disengage tab 328 from the wound retractor.

Clamp 308 is an annular forming an aperture/channel that is configured to align with the aperture/channel formed by sleeve 102 through the incision in the body wall. Clamp body 324 is generally cylindrical and includes a circular outer periphery. Clamp body 324 is sized and shaped to fit onto wound retractors in accordance with this disclosure (e.g., wound retractor 100). The diameter of clamp body 324 can be selected to be greater than a diameter of the portion of the wound retractor to which clamp 308 is to be connected. However, lever 326 and tab 328 may have portions (e.g., a tapered surface/ramp) that present a diameter that is less than the diameter of the wound retractor. As will be described in more detail below, thus, the periphery of clamp body 324 other than at lever 326 and tab 328 can be configured to fit onto the wound retractor and lever 326 and tab 328 can be configured to snap and lock onto the wound retractor.

Clamp body 324 including tab 328, lever 326, and gasket 330 can be fabricated from a variety of materials. Clamp body can be made from a variety of polymers, including, for example, polycarbonate or a rigid thermoplastic polyurethane (TPU). Lever 326 can also be made from a variety of polymers, including, for example, a polycarbonate. And, gasket 330 can be made from a variety of soft (flexible, deformable, etc.) material with sealing properties, including, for example, a silicone gel, an elastomer (e.g., a soft rubber), or a soft foam.

Gasket 330 needs to be configured to seal between the irregular shape of wound retractor 100 with sleeve 102 wrapped around proximal ring 106 and an access port assembly (for example, including a clamp as described below). Because the rolled wound retractor 100 may be wrinkled and may be rolled to different heights, gasket 330 may need to be conformable to fill the gaps with the wound retractor and be soft, or have a low spring rate, so it does not require excessive force to compress the gasket during coupling. Because there is a fairly large range of rolled wound retractor heights based on anatomy and the amount of rolling, the softer the spring of gasket 330, the more consistent the required clamping force will be. Additionally, in examples, gasket 330 is configured to withstand the sterilization process and may be fabricated from biocompatible materials.

Figure 3E:
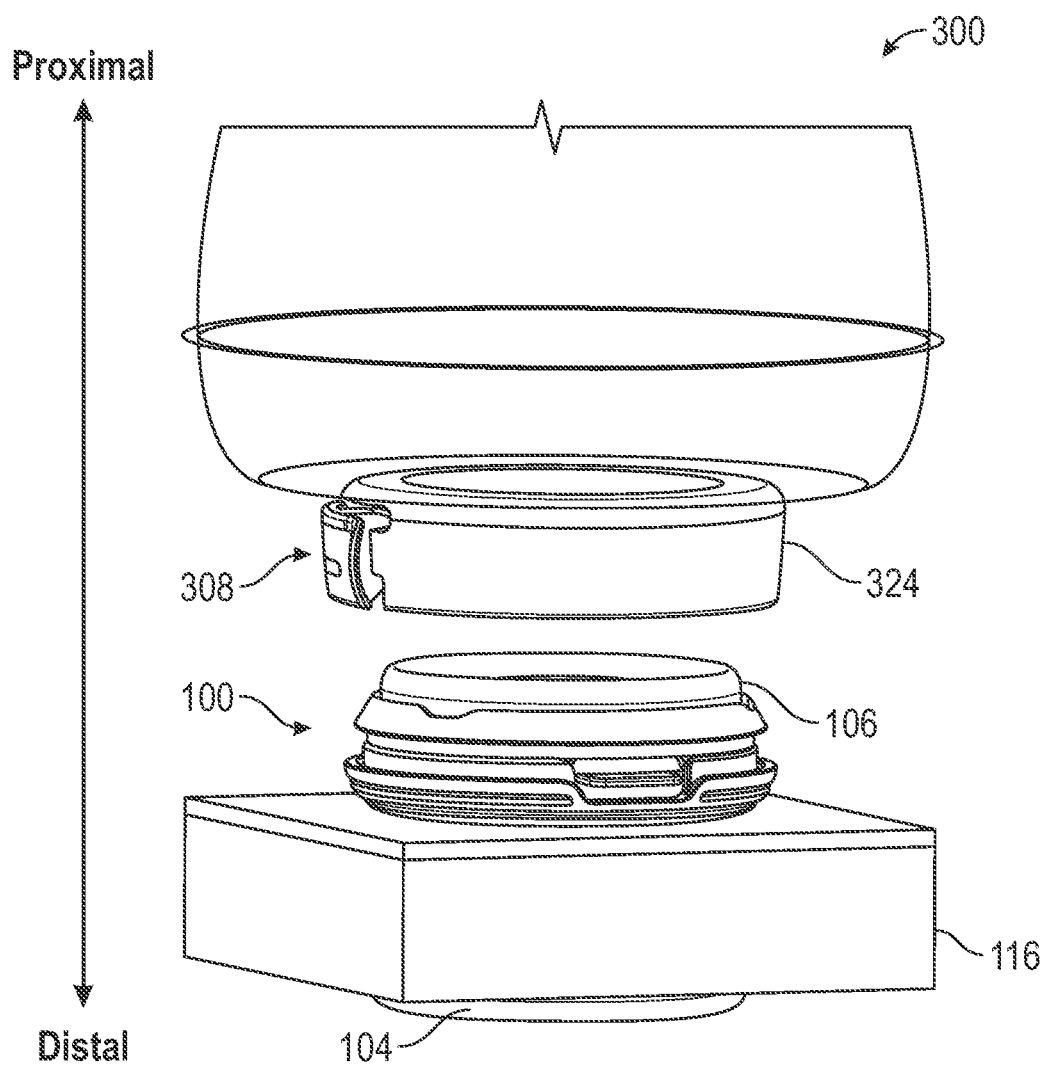
Figure 3F:
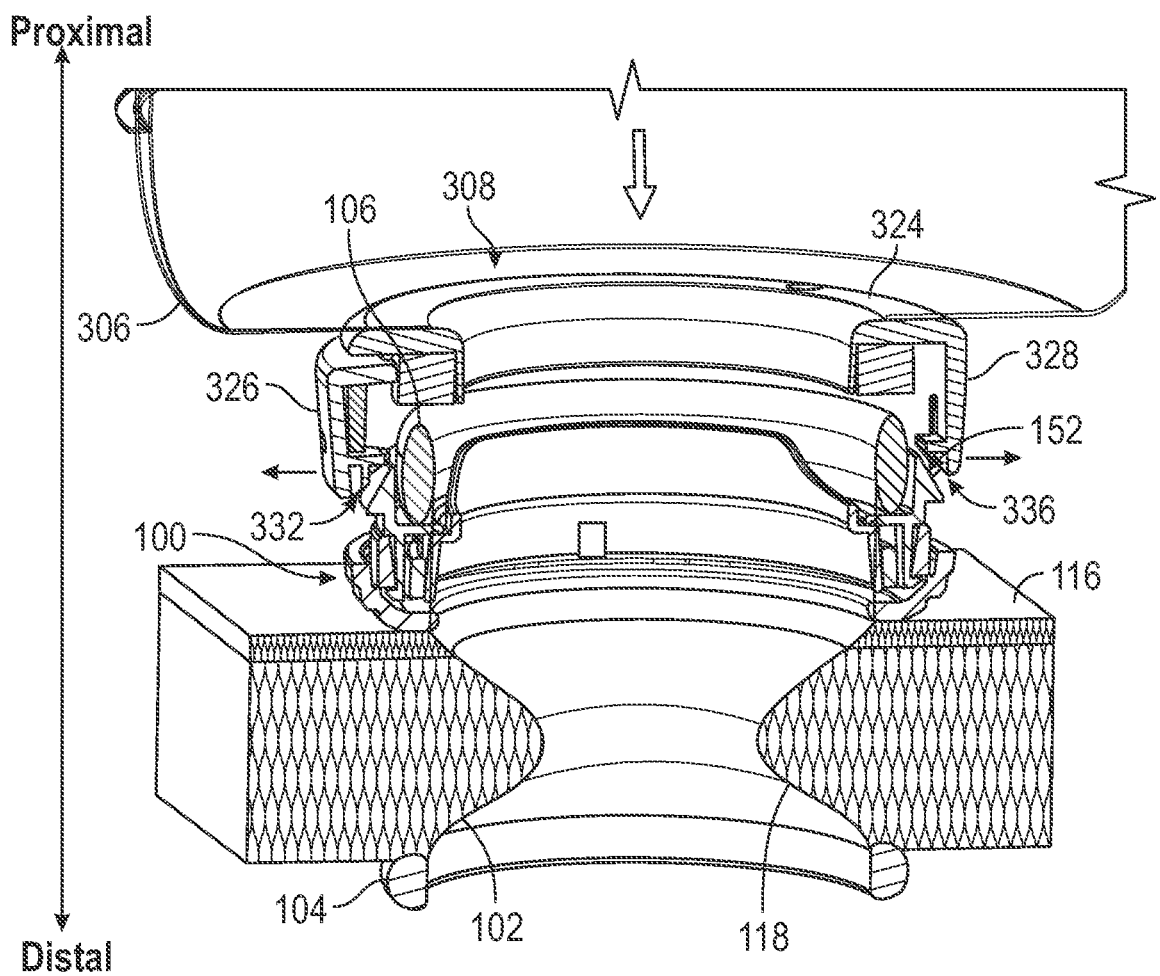
Figure 3G:
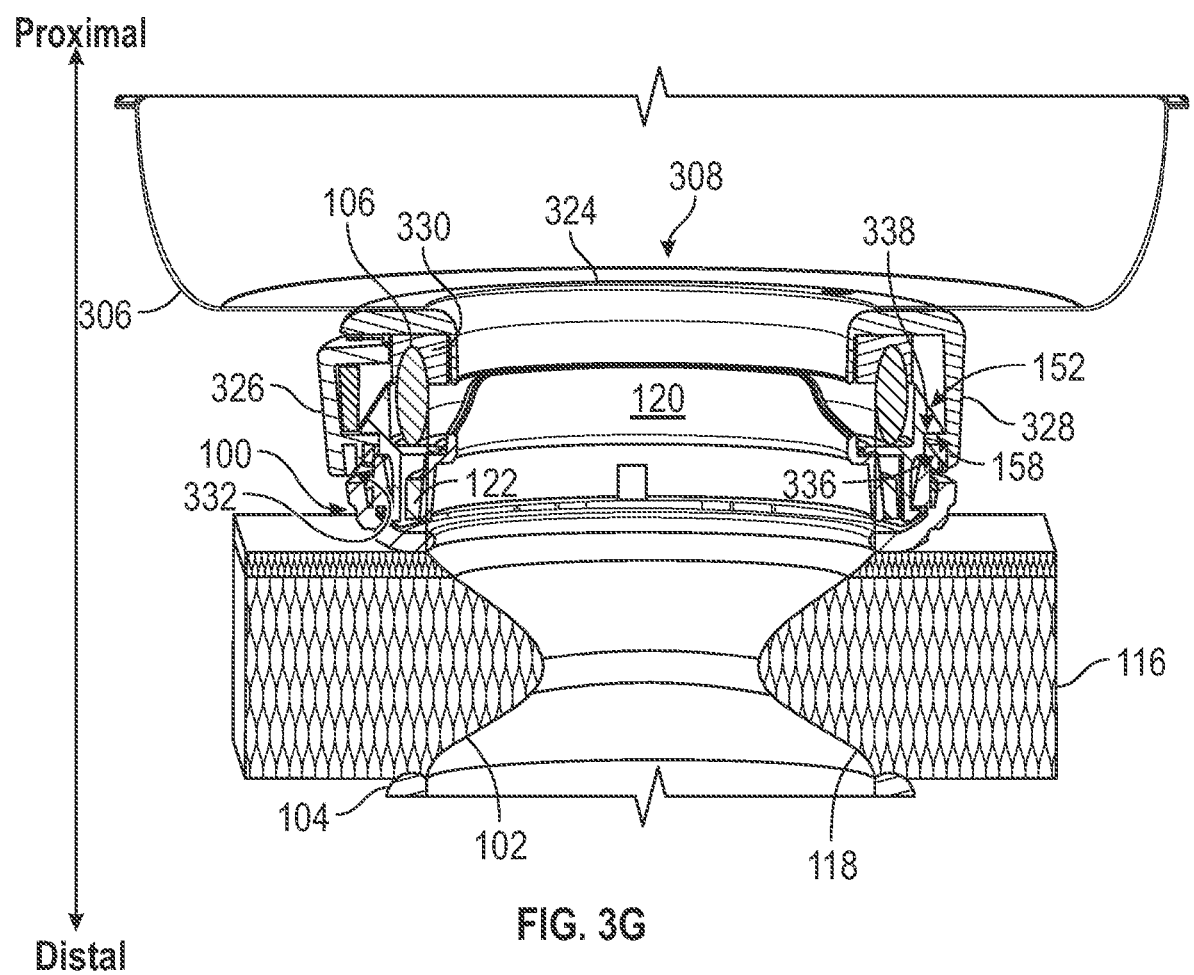

FIGS. 3E-3G depict connecting clamp 308 (connected to access port device 300) to wound retractor 100. FIG. 3E depicts access port device 300 connected to example clamp 308 being positioned above (proximal to) wound retractor 100 to roughly align clamp 308 and wound retractor 100. FIG. 3F depicts clamp 308 as it begins to engage and be connected to wound retractor 100. FIG. 3G depicts clamp 308 and access port device 300 connected to wound retractor 100.

Referring to FIG. 3F, as clamp 308 begins to engage wound retractor 100, tapered surface 152 of proximal housing section 124 engages tapered surface 332 of lever 326 and tapered surface 336 of tab 328, which, in turn, causes lever 326 and tab 328 to deflect radially outward. The portions of the outer circumference/periphery of clamp body 324 of clamp 308 other than at lever 326 and tab 328 have a diameter that is larger than the outside diameter of proximal housing section 124. Tapered surface 332 of lever 326 and tapered surface 336 of tab 328 are the mechanism by which clamp 308 can be snapped onto wound retractor 100.

Referring to FIG. 3G, clamp 308 (and access port device 300 connected thereto) are connected to wound retractor 100. After lever 326 and tab 328 have deflected around tapered surface 152 of proximal housing section 124 of wound retractor 100, lip 334 of lever 326 and lip 338 of tab 328 catch on lip 158 of proximal housing section 124 to secure clamp 308 to wound retractor 100. Lever 326 and tab 328 may be flexible and resilient to allow them to deflect radially outward around tapered surface 152 and to snap back radially inward to engage lip 158 of proximal housing section 124. Additionally, as lever 326 is flexible and resilient, a clinician can engage a portion of lever 326 to deflect the lever radially outward to remove clamp 308 from wound retractor 100. In this manner, clamp 308 can be quickly and easily connected and disconnected from a wound retractor in accordance with this disclosure.

FIG. 3H is a detailed view depicting clamp 308 connected to wound retractor 100. In FIG. 3H, clamp 308 is removably locked onto wound retractor 100. In this position, unlock tabs 142 (and 140 not visible in this detailed view) of outer ring 106 of auto-lock collar 108 protrude out underneath a distal end of clamp 308. The clearance between the proximal face of unlock tab 142 and the distal end of clamp 308 is relatively small. In this way, the proximal end of clamp 308 connected to wound retractor 100 acts as a mechanical stop against movement of unlock tab 142 (and 140) in the proximal direction. Clamp 308 thereby reduces the amount of unintended movement of unlocking tabs 140 and 142. For example, if access port device 300 is tilted during a procedure and the skin of the patient puts upward (proximal) pressure on tabs 140 and 142, clamp 308 will not become accidentally unlocked from wound retractor 100.

As can be seen in FIG. 3H, gasket 330 of clamp 308 forms a seal around sleeve 102 wrapped around proximal ring 106 of wound retractor 100. Thus, gasket 330 may form part or all of the structure that seals the connection between wound retractor 100 and clamp 308 that is necessary to maintain insufflation pressure. Gasket 330, in this example, is a ring shaped gasket with a rectilinear cross-sectional profile. In another example, gasket 330 could have a different shape and/or configuration. For example, gasket 330 may be implemented as an O-ring with a curved or circular cross-sectional profile. In an example, gasket 330 may be formed as a U-shaped gasket. The U-shaped gasket 330, whether disposed in clamp 308 right-side up or upside down, may, for example, be configured to hug the shape of sleeve 102 wrapped around proximal ring 106 or may form a relieved profile that can be more easily compressed when connecting clamp 308 to wound retractor 100.

Figure 4A:
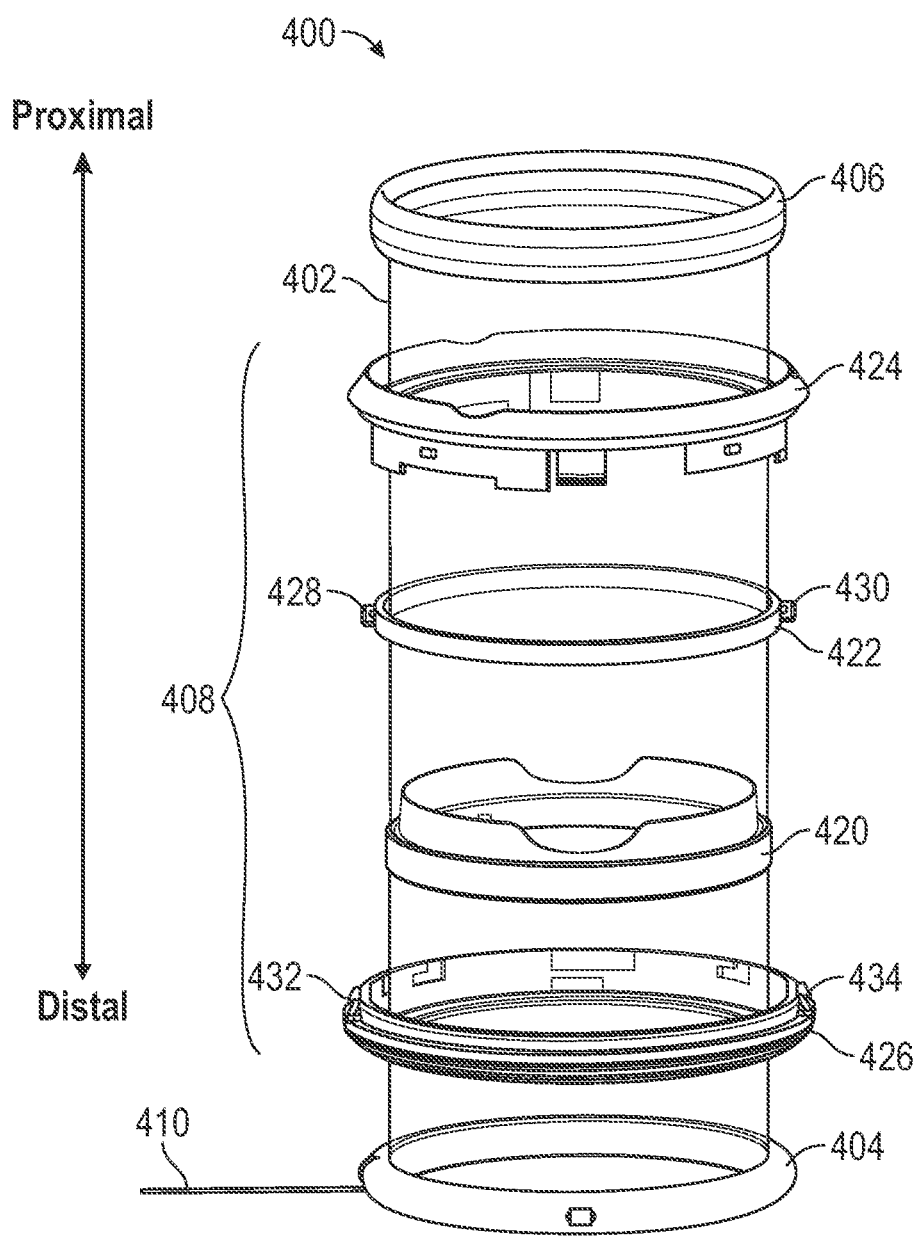
FIG. 4A is a perspective view depicting another example wound retractor in accordance with this disclosure.

FIG. 4A is a perspective view depicting another example wound retractor 400 in accordance with this disclosure. In FIG. 4A, wound retractor 400 includes sleeve 402 having distal ring 404 and proximal ring 406, auto-locking collar 408, removal tether 410 and removal ring (not shown). Auto-locking collar 408 includes inner ring 420, outer ring 422, proximal housing section 424, and distal housing section 426. Inner ring 420 is inside and generally concentrically arranged with sleeve 402. Outer ring 422 is outside and generally concentrically arranged with sleeve 402. And, proximal and distal housing sections 424 and 426 are outside and generally concentrically arranged with sleeve 402. Proximal and distal housing sections 424 and 426 are configured to be removably coupled to one another to capture inner ring 420 and outer ring 422.

Wound retractor 400 is substantially similar in structure, arrangement, function, etcetera to example wound retractor 100, except that wound retractor 400 includes a different mechanism for releasing auto-locking collar 408. As such, the details of outer ring 422 and distal housing section 426 will be described with reference to this example without repeating a description of sleeve 402, distal and proximal rings 404 and 406, inner ring 420 or proximal housing section 424, which can be substantially similar to the corresponding components of example wound retractor 100.

Auto-locking collar 408 is disposed along sleeve 402 between distal ring 404 and proximal ring 406. Auto-locking collar 408 is configured to freely slide along sleeve 402 in one direction and to automatically lock against movement along sleeve in an opposite direction. For example, in the example of FIG. 4A, collar 408 is configured to slide in a direction from proximal to distal ends of sleeve 402 to draw collar 408 closer to the site of an incision and closer to distal ring 404. Auto-locking collar 408 is also configured to automatically lock against movement of the collar in a direction from distal to proximal ends of sleeve 402. Collar 408 is configured to slide down sleeve 402 to be seated outside of the incision and against the outer surface of a body wall in which the incision is made. Collar 408 can be slid down against the body wall and can be automatically locked in place to apply a force on sleeve 402 as the sleeve is tensioned between collar 408 and distal ring 404. Tensioning sleeve 402 between collar 408 and distal ring 404 applies a retraction force on and thereby dilates the incision.

Auto-locking collar 408 includes inner ring 420 inside sleeve 402. Inner ring 402 includes a tapered outer surface, which increases in diameter from a proximal end of the inner ring toward a distal end of the inner ring. Auto-locking collar 408 also includes outer ring 422 outside sleeve 402. Outer ring 422 includes a tapered inner surface. The tapered inner surface of outer ring 422 increases in diameter from a proximal end of the outer ring toward a distal end of the outer ring. A portion of sleeve 402 is captured between the tapered outer surface and the tapered inner surface. Auto-locking collar 408 is configured to slide along sleeve 402 in a proximal-to-distal direction without causing the tapered outer surface and the tapered inner surface to lock onto sleeve 402. In response to a tensioning force on sleeve 402, however, the tapered outer surface and the tapered inner surface are configured to automatically lock onto the sleeve and to prevent collar 408 from moving relative to sleeve 402.

Outer ring 422 includes at least one unlock tab 428 extending radially outward from the outer ring. In the example of FIG. 4A, outer ring 422 includes first unlock tab 428 extending radially outward from outer ring 422 and second unlock tab 430 extending radially outward from outer ring 422. First unlock tab 428 is diametrically opposed to second unlock tab 430. Unlock tabs 428 and 430 (together or separately) are configured to unlock inner ring 420 and outer ring 422 from sleeve 402 in response to a force on the unlock tab(s) in a direction from the distal end of sleeve 402 toward the proximal end of sleeve 402 (or, more generally, in response to a force in a distal-to-proximal direction).

Unlike the example of unlock tabs 140 and 142 of example wound retractor 100, however, unlock tabs 428 and 430 are not configured to be directly engaged by a user, but, instead are configured to be engaged by buttons 432 and 434 in distal housing section 426 when a user presses the buttons. Thus, after auto-locking collar 408 is slid down to engage the body wall and tension sleeve 402 and outer ring 422 moves into to the distal locked position, a clinician can adjust wound retractor 400 by simply depressing buttons 432 and 434, which engages unlock tabs 428 and 430 in a distal-to-proximal direction to unlock inner and outer rings 420 and 422 and release auto-locking collar 408 to slide proximally along sleeve 402.

Figure 4B:
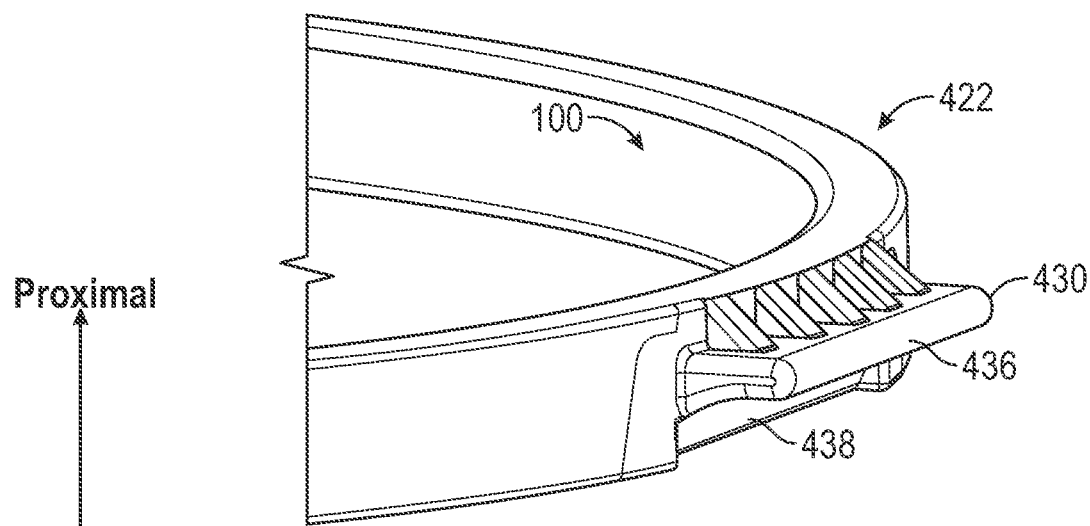
FIGS. 4B and 4C are detail views of an outer ring and distal housing section of the example wound retractor of FIG. 4A.
Figure 4C:
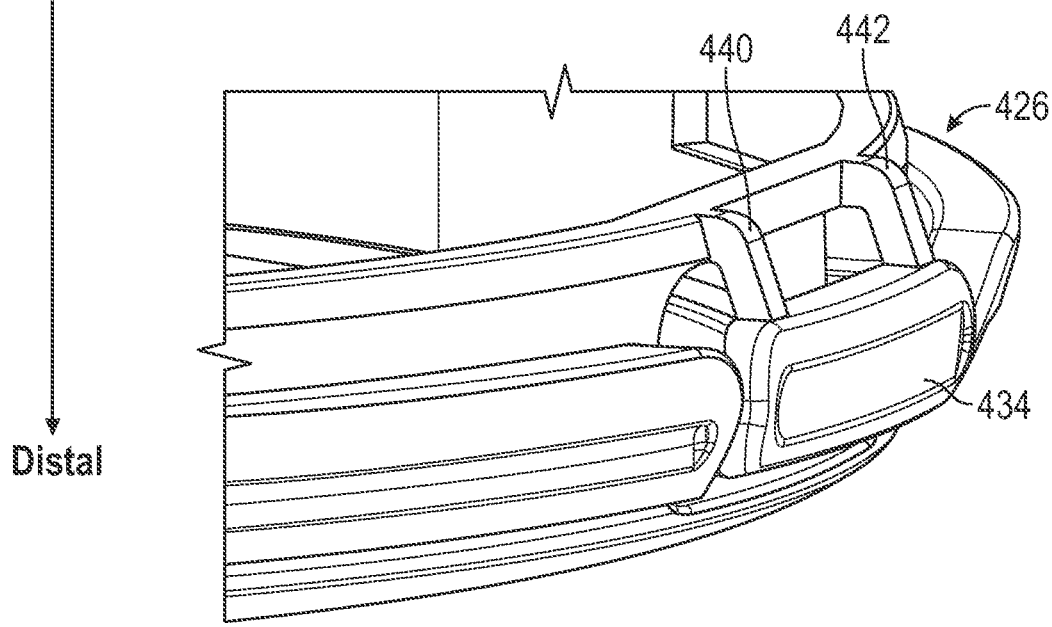

FIGS. 4B and 4C are detail views of outer ring 422 and distal housing section 426 of wound retractor 400. In FIG. 4B, unlock tab 430 includes radially outwardly extending flange 436 with a distal or underside convex curved surface 438. Although unlock tab 428 is not depicted in this detail view it is structured, shaped, and sized the same as unlock tab 430. In FIG. 4C, button 434 is hingedly coupled to distal housing section 426 by resilient links 440 and 442 (although two links are employed in this example, other examples can include more or fewer resilient links for such hinged connection). Although button 432 is not depicted in this detail view it is structured, shaped, sized, and connected in the same manner as button 434.

Figure 4D:
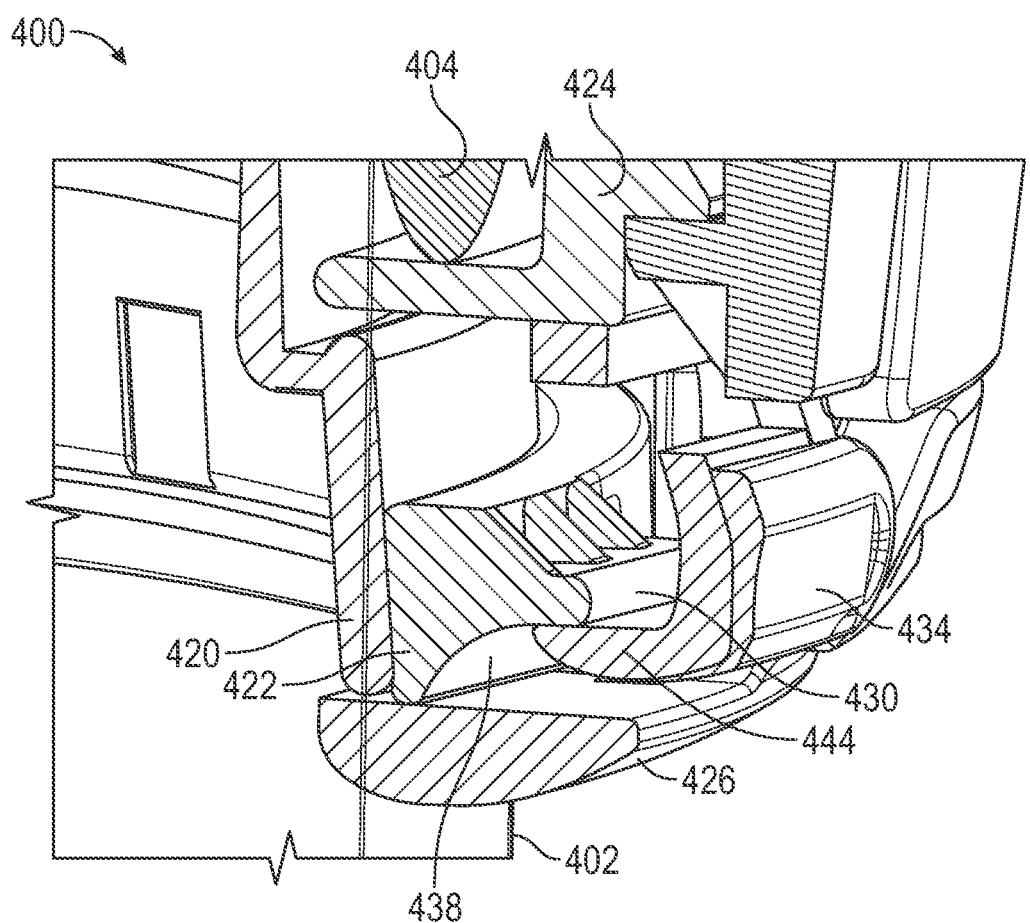
FIG. 4D is a section view of the auto-locking collar of wound retractor of FIG. 4A.

FIG. 4D is a section view of auto-locking collar 408 of wound retractor 400. In FIG. 4D, inner ring 420 is interlocked with outer ring 422 capturing sleeve 402 therebetween. Additionally, inner ring 420 and outer ring 422 are captured by/in proximal housing section 424 and distal housing section 426. In this view, additional details of unlock tab 430 and button 434 are illustrated. For example, the profile of distal convex curved surface 438 is depicted. Additionally, the complementary profile of button 434 is depicted, which includes a radially inwardly extending L-shaped flange 444. As illustrated in FIG. 4D, the base of L-shaped flange 444 extends radially inwardly to engage distal surface 438 of unlock tab 430.

Figure 4G:
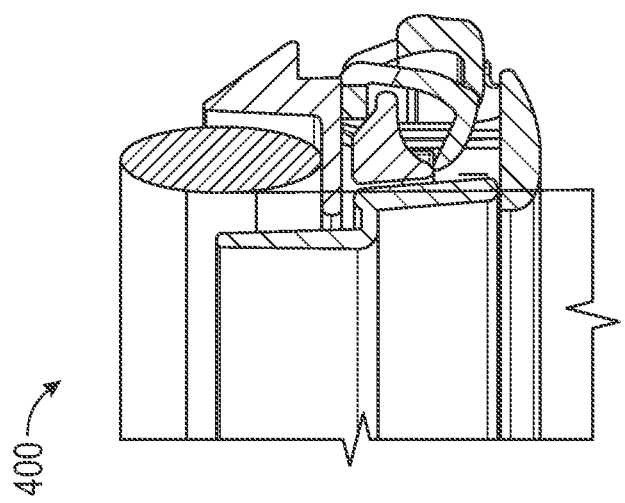
FIGS. 4E-4G are section detail views of the wound retractor of FIG. 4A.
Figure 4F:
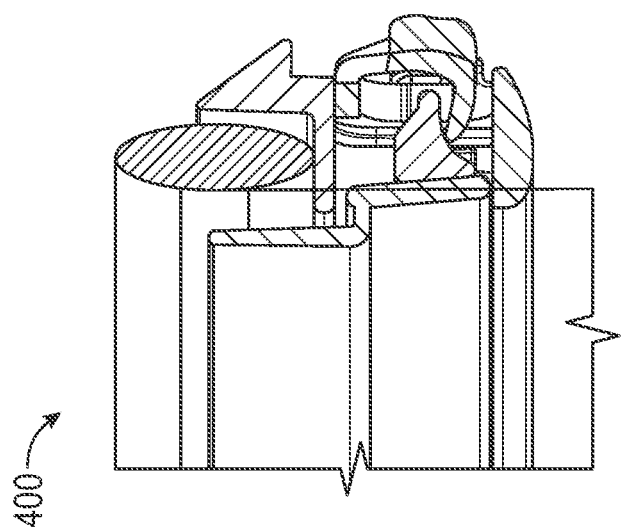
Figure 4E:
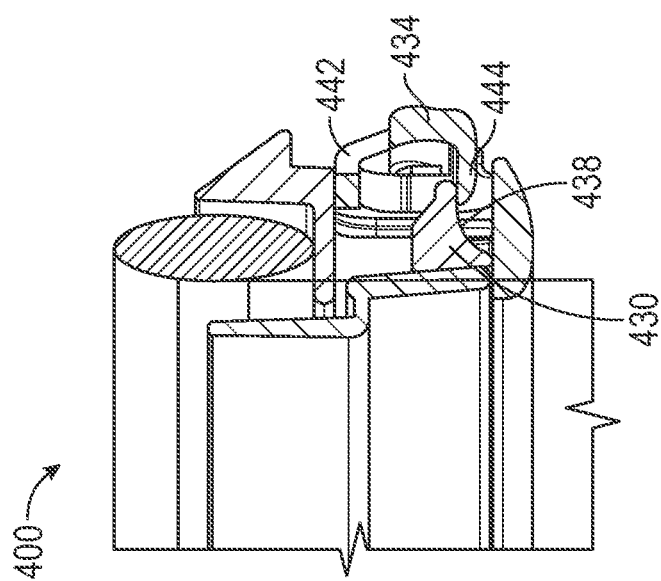

FIGS. 4E-4F are section detail views of wound retractor 400 depicting button 434 being depressed (pushed radially inwardly) to engage unlock tab 430 in a distal-to-proximal direction to unlock inner and outer rings 420 and 422 and release auto-locking collar 408 to slide along sleeve 402. The shape and size of L-shaped flange 444 of button 434 and distal convex curved surface 438 of unlock tab 430 have been selected such that the amount tab 430 is displaced in a distal-to-proximal direction increases as flange 444 is displaced by button 434 being depressed. In other words, in the initial condition shown in FIG. 4E, the user commencing to depress button 434 causes mostly a radially inward movement of flange 444 and relatively less movement of flange 444, and thereby tab 430 in the distal-to-proximal direction. As the user continues to depress button 434 in FIGS. 4F and 4G, however, movement of flange 444 decreases in the radially inward direction and increases in the distal-to-proximal direction.

Persons of skill in the art will understand that any of the features described above may be combined with any of the other example features, as long as the features are not mutually exclusive. All possible combinations of features are contemplated, depending on clinical or other design requirements.

The examples (e.g., methods, systems, or devices) described herein may be applicable to surgical procedures, non-surgical medical procedures, diagnostic procedures, cosmetic procedures, and non-medical procedures or applications. The examples may also be applicable for training, or for obtaining information, such as imaging procedures. The examples may be applicable to handling of tissue that has been removed from human or animal anatomies and will not be returned to a human or animal, or for use with human or animal cadavers.

The above detailed description includes references to the accompanying drawings, which form a part of the detailed description. The drawings show, by way of illustration, specific embodiments in which the invention may be practiced. These embodiments are also referred to herein as "examples." Such examples may include elements in addition to those shown or described. But, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round", a component that is not precisely circular (e.g., one that is slightly oblong or is a many-sided polygon) is still encompassed by this description. Coordinate systems or reference frames are provided for aiding explanation, and implantations may use other reference frames or coordinate systems other than those described herein.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the invention should be determined with reference to the appended claims, along with the full scope of equivalents to which such claims are entitled.

The invention claimed is:

1. A wound retractor comprising:
a sleeve comprising a proximal end and a distal end;
an inner ring inside the sleeve between the proximal and distal ends of the sleeve, the inner ring comprising an inner ring proximal end, an inner ring distal end, and a tapered outer surface that increases in diameter from the inner ring proximal end toward the inner ring distal end; and
an outer ring outside the sleeve between the proximal and distal ends of the sleeve, the outer ring comprising an outer ring proximal end, an outer ring distal end, and a tapered inner surface opposing the tapered outer surface of the inner ring and that increases in diameter from the outer ring proximal end toward the outer ring distal end;
wherein a portion of the sleeve is captured between the tapered outer surface of the inner ring and the tapered inner surface of the outer ring.

2. The wound retractor of claim 1, wherein:
the inner ring and the outer ring are configured to slide together in a direction from the proximal end of the sleeve toward the distal end of the sleeve without the tapered outer surface of the inner ring and the tapered inner surface of the outer ring locking onto the sleeve.

3. The wound retractor of claim 1, wherein:
the tapered outer surface of the inner ring and the tapered inner surface of the outer ring are configured to lock onto the sleeve in response to a force from the sleeve in a direction from the proximal end of the sleeve toward the distal end of the sleeve.

4. The wound retractor of claim 1, wherein:
the inner ring comprises a conical section and a cylindrical section joined to the conical section; and
the conical section comprises the tapered outer surface of the inner ring.

5. The wound retractor of claim 4, wherein:
the cylindrical section is proximal to the conical section.

6. The wound retractor of claim 4, wherein:
the conical section is joined to the cylindrical section by a ledge that extends radially inward from the conical section to join to the cylindrical section.

7. The wound retractor of claim 4, wherein:
a maximum outer diameter of the cylindrical section is less than a minimum outer diameter of the conical section.

8. The wound retractor of claim 1, wherein:
the inner ring comprises at least one circumferential notch.

9. The wound retractor of claim 1, wherein:
the inner ring comprises a first circumferential notch and a second circumferential notch; and
the first circumferential notch is diametrically opposite the second circumferential notch.

10. The wound retractor of claim 1, wherein:
the wound retractor further comprises a housing; and
the inner ring and the outer ring are captured within the housing.

11. The wound retractor of claim 10, wherein:
the housing comprises a proximal housing section and a distal housing section coupled to one another; and
the proximal housing section and the distal housing section are outside the sleeve.

12. The wound retractor of claim 11, wherein:
the proximal housing section comprises one of a tab and a slot;
the distal housing section comprises the other of the tab and the slot; and
the proximal and distal housing sections are removably coupled to one another by the tab engaged with the slot.

13. The wound retractor of claim 11, wherein:
the proximal housing section comprises:
a proximal end;
a distal end;
a tapered outer surface that increases in diameter from the proximal end of the proximal housing section toward the distal end of the proximal housing section;
a cylindrical section proximal to the tapered outer surface; and
a lip extending radially inward from a distal end of the tapered outer surface to the cylindrical section.

14. The wound retractor of claim 13, wherein:
the proximal housing section further comprises a ledge extending radially inward from the cylindrical section.

15. The wound retractor of claim 11, wherein:
the distal housing section comprises first and second buttons hingedly coupled to the distal housing section and diametrically opposite one another;
the outer ring comprises a first unlock tab and a second unlock tab diametrically opposite the first unlock tab; and
the first and second buttons are configured to be depressed to apply force on the first and second unlock tabs to unlock the tapered outer surface of the inner ring and the tapered inner surface of the outer ring from the sleeve.

16. The wound retractor of claim 15, wherein:
each of the first and second buttons comprises a flange that extends radially inward from the button;
each of the first and second unlock tabs comprise a flange extending radially outward from the outer ring and having a distal convex surface; and
the flange of each of the first and second buttons is configured to push against and slide along the distal convex surface of each of the first and second unlock tabs on condition the first and second buttons are depressed.

17. The wound retractor of claim 1, wherein:
the outer ring comprises a first unlock tab and a second unlock tab diametrically opposite the first unlock tab;
the first and second unlock tabs extend radially outward from the outer ring; and
the first and second unlock tabs are configured such that force on the first and second unlock tabs in a direction from the distal end of the sleeve toward the proximal end of the sleeve unlocks the tapered outer surface of the inner ring and the tapered inner surface of the outer ring from the sleeve.

18. The wound retractor of claim 1, wherein:
the sleeve further comprises a proximal ring, a distal ring, and an outer surface;
the distal ring is connected to the distal end of the sleeve; and
the proximal ring is connected to the proximal end of the sleeve and comprises an oblate shape having a flat inner surface connected to the outer surface of the sleeve.

19. A medical device comprising:
a wound retractor and an access port assembly;
the wound retractor comprising a sleeve, an inner ring inside the sleeve, an outer ring outside the sleeve, and a housing in which the inner and outer rings are captured;
the inner ring comprising a tapered outer surface having a proximal diameter and a distal diameter, the proximal diameter of the tapered outer surface being less than the distal diameter of the tapered outer surface;
the outer ring comprising a tapered inner surface having a proximal diameter and a distal diameter, the proximal diameter of the tapered inner surface being less than the distal diameter of the tapered inner surface, a portion of the sleeve being captured between the tapered outer surface of the inner ring and the tapered inner surface of the outer ring; and
the access port assembly comprising:
an envelope comprising a distal end; and
a clamp connected to the distal end of the envelope and configured to be connected to the housing of the wound retractor.

20. A medical device for which a distal direction is defined towards a patient and a proximal direction is defined away from the patient, the medical device comprising:
an inner ring comprising an outer surface tapering outward in the distal direction;
an outer ring surrounding the inner ring and comprising an inner surface tapering outward in the distal direction and opposing the outer surface of the inner ring; and
a wound retractor sleeve captured between the outer surface of the inner ring and the inner surface of the outer ring.

\* \* \* \* \*